(12) United States Patent
Haynes et al.

(10) Patent No.: US 9,333,098 B2
(45) Date of Patent: May 10, 2016

(54) PROSTHETIC DEVICE UTILIZING ELECTRIC VACUUM PUMP

(75) Inventors: Michael L. Haynes, Columbus, OH (US); Mark W. Ford, Jamestown, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 199 days.

(21) Appl. No.: 13/231,690

(22) Filed: Sep. 13, 2011

(65) Prior Publication Data

US 2012/0004737 A1    Jan. 5, 2012

Related U.S. Application Data

(60) Division of application No. 11/688,402, filed on Mar. 20, 2007, now Pat. No. 8,016,892, which is a continuation-in-part of application No. 11/423,632, filed on Jun. 12, 2006, now Pat. No. 7,947,085, which is a continuation-in-part of application No. 11/149,858, filed on Jun. 10, 2005, now Pat. No. 7,914,586.

(51) Int. Cl.
*A61F 2/48* (2006.01)
*A61F 2/80* (2006.01)
(Continued)

(52) U.S. Cl.
CPC ... *A61F 2/68* (2013.01); *A61F 2/80* (2013.01); *A61F 2/5044* (2013.01); *A61F 2/54* (2013.01); *A61F 2/60* (2013.01); *A61F 2/70* (2013.01); *A61F 2/76* (2013.01); *A61F 2002/30591* (2013.01); *A61F 2002/5032* (2013.01); *A61F 2002/5083* (2013.01); *A61F 2002/701* (2013.01); *A61F 2002/702* (2013.01);
(Continued)

(58) Field of Classification Search
CPC ........ A61F 2002/742; A61F 2/68; A61F 2/70
USPC ...................................................... 623/34, 24
See application file for complete search history.

(56) References Cited

U.S. PATENT DOCUMENTS 2,478,721 A    8/1949  Stewart
3,683,239 A *  8/1972  Sturman ....................... 361/194
(Continued)

FOREIGN PATENT DOCUMENTS

WO    2006135851    12/2006

OTHER PUBLICATIONS

International Search Report for WO 2006135851 mailed Jan. 10, 2007.

(Continued)

*Primary Examiner* — Jacqueline Woznicki
(74) *Attorney, Agent, or Firm* — Benesch Friedlander Coplan & Aronoff, LLP; Benjamen E. Kern; Eric S. Foster

(57) ABSTRACT

A prosthetic assembly operative to evacuate an interior of a prosthetic socket, and control systems for use therewith. The prosthetic assembly employs evacuation devices for evacuating the socket. The evacuation devices preferably include at least an electrically powered vacuum pump and a power source located within a housing. Associated control systems may be of various design and may employ wired or wireless communication. When wireless communication is employed, a hand held controller or other remote control device may be used to remotely control operation of the evacuation device.

19 Claims, 24 Drawing Sheets

(51) Int. Cl.
*A61F 2/68* (2006.01)
*A61F 2/70* (2006.01)
*A61F 2/74* (2006.01)
*A61F 2/50* (2006.01)
*A61F 2/54* (2006.01)
*A61F 2/60* (2006.01)
*A61F 2/76* (2006.01)
*A61F 2/30* (2006.01)

(52) U.S. Cl.
CPC .... *A61F 2002/704* (2013.01); *A61F 2002/705* (2013.01); *A61F 2002/707* (2013.01); *A61F 2002/74* (2013.01); *A61F 2002/742* (2013.01); *A61F 2002/747* (2013.01); *A61F 2002/764* (2013.01); *A61F 2002/768* (2013.01); *A61F 2002/769* (2013.01); *A61F 2002/7635* (2013.01); *A61F 2002/802* (2013.01); *A61F 2002/805* (2013.01)

(56) References Cited

U.S. PATENT DOCUMENTS

| | | | |
|---|---|---|---|
| 3,683,423 | A | 8/1972 | Crapanzano |
| 5,658,353 | A | 8/1997 | Layton |
| 5,807,397 | A | 9/1998 | Barreras |
| 5,840,047 | A | 11/1998 | Stedham |
| 5,888,212 | A | 3/1999 | Petrofsky et al. |
| 6,063,125 | A | 5/2000 | Arbogast et al. |
| 6,137,889 | A | 10/2000 | Shennib et al. |
| 6,287,345 | B1 | 9/2001 | Slemker |
| 6,508,842 | B1 | 1/2003 | Caspers |
| 6,517,585 | B1 * | 2/2003 | Zahedi et al. .......... 623/24 |
| 6,554,868 | B1 | 4/2003 | Caspers |
| 6,585,774 | B2 | 7/2003 | Dean, Jr. et al. |
| 6,610,096 | B2 | 8/2003 | MacDonald |
| 6,645,253 | B2 | 11/2003 | Caspers |
| 6,726,726 | B2 | 4/2004 | Caspers |
| 6,905,519 | B2 | 6/2005 | Swanson, Sr. |
| 6,926,742 | B2 | 8/2005 | Caspers et al. |
| 6,974,484 | B2 | 12/2005 | Caspers |
| 7,029,500 | B2 | 4/2006 | Martin |
| 7,914,586 | B2 | 3/2011 | Haines |
| 7,947,085 | B2 | 5/2011 | Haines et al. |
| 8,016,892 | B2 | 9/2011 | Colvin et al. |
| 8,652,217 | B2 | 2/2014 | Haynes et al. |
| 2002/0087215 | A1 | 7/2002 | Caspers |
| 2002/0198604 | A1 * | 12/2002 | Schulman et al. ........ 623/25 |
| 2003/0181990 | A1 | 9/2003 | Phillips |
| 2004/0019382 | A1 | 1/2004 | Amirouche et al. |
| 2004/0030411 | A1 | 2/2004 | Caspers |
| 2004/0143345 | A1 | 7/2004 | Caspers |
| 2004/0181290 | A1 | 9/2004 | Caspers |
| 2004/0260403 | A1 | 12/2004 | Patterson et al. |
| 2005/0283257 | A1 * | 12/2005 | Bisbee et al. ............ 623/24 |
| 2006/0135851 | A1 | 6/2006 | Yamazaki |
| 2006/0212128 | A1 | 9/2006 | Nachbar |
| 2006/0229736 | A1 | 10/2006 | Christensen |
| 2006/0282174 | A1 | 12/2006 | Haines |
| 2007/0027555 | A1 | 2/2007 | Palmer et al. |
| 2007/0055383 | A1 * | 3/2007 | King ............................ 623/34 |
| 2007/0112439 | A1 | 5/2007 | Panucialman |
| 2007/0191965 | A1 | 8/2007 | Colvin et al. |
| 2008/0086218 | A1 | 4/2008 | Egilsson |
| 2008/0147204 | A1 | 6/2008 | Ezenwsa |
| 2009/0281637 | A1 * | 11/2009 | Martin ........................ 623/34 |

OTHER PUBLICATIONS

International Preliminary Report on Patentability Chapter 1 for WO 2006135851 issued Dec. 11, 2007.
Written Opinion for WO 2006135851 issued Dec. 10, 2007.
Supplemental Partial European Search report for EP 1887991 issued Aug. 18, 2010.
Communication pursuant to 94(3) from Examining division for EP 1887991 issued May 24, 2011.
Communication pursuant to 94(3) from Examining division for EP 1887991 issued Feb. 6, 2013.
US 5,761,742, 07/2004, Caspers (withdrawn)

* cited by examiner

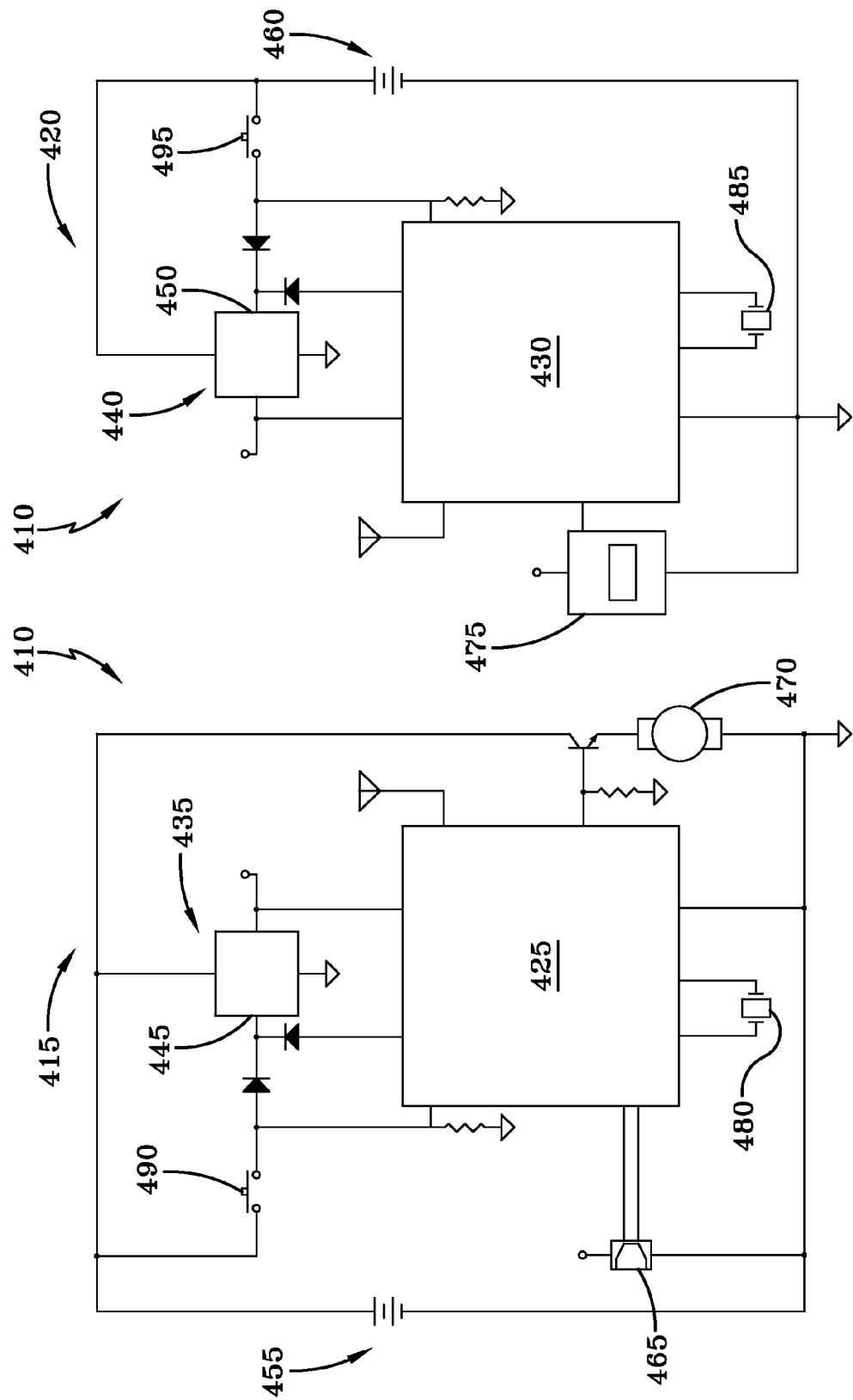

PROSTHETIC DEVICE UTILIZING ELECTRIC VACUUM PUMP

The present application is a division of U.S. patent application Ser. No. 11/688,402, filed on Mar. 20, 2007, now U.S. Pat. No. 8,016,892, issued Sep. 13, 2011, which is a continuation-in-part of U.S. patent application Ser. No. 11/423,632, filed on Jun. 12, 2006, now U.S. Pat. No. 7,947,085, issued May 24, 2011, which is a continuation-in-part of U.S. patent application Ser. No. 11/149,858, filed on Jun. 10, 2005, now U.S. Pat. No. 7,914,586 issued May 29, 2011.

BACKGROUND OF THE INVENTION

The present invention is directed to electrically-powered evacuation devices for use in evacuating a prosthetic socket and/or to prosthetic limbs incorporating such electrically-powered evacuation devices. The present invention is also directed to various systems and methods for configuring, monitoring, performing, adjusting and controlling such devices.

Artificial limbs have been in use throughout history, having been first recorded circa 2750 B.C. During that period of time, interfacing and suspending an artificial limb has been a continuing challenge. Various and numerous theories and anatomical constructs have been used over time in an evolving manner, and these have revealed a number of key factors in maximizing comfort and functional potential for persons who wear artificial limbs.

Firstly, the surgical procedure used to perform limb amputation is an important factor. The size and shaping of the patient's residual limb is often important to the comfort the patient will later have with a prosthesis. Stated simply, it is critical that the residual limb and prosthesis interface tightly and couple and distribute pressure evenly across the surface of the residual limb.

Early versions of artificial limbs required the use of leather or equivalent straps or belts to suspend the artificial limb upon the person. Later systems employed linkage techniques such as condylar wedges, rubber or synthetic elastic tubing, thermoplastic roll-on sleeves with pin locking systems, and sub-atmospheric pressure. Of these, sub atmospheric pressure is typically often preferred, because it creates a linkage that provides maximum proprioceptive feedback and control for the artificial limb user. It also provides the best linkage between the user's limb and the prosthetic device.

Creating a reliable sub atmospheric pressure chamber between the residual limb and prosthetic device has, however, proved to be a challenge. As new airtight thermoplastic and thermo set materials have evolved, along with airtight thermoplastic roll-on liners, the potential for creating a sub-atmospheric pressure within the prosthetic chamber (socket) has improved. Specifically, the patient's residual limb is covered with a roll-on urethane, silicone, or other thermoplastic or theromoset liner, which helps to protect the user's tissue from unwanted isolated high negative pressure values, and provides cushioning for the tissue at the same time. The liner also helps to distribute the sub-atmospheric pressure applied to the users limb in a more uniform manner.

Several mechanical means for creating an elevated negative pressure chamber within a prosthetic socket have emerged. One method disclosed in U.S. Pat. No. 6,554,868, utilizes a weight activated pump, in which sub atmospheric pressure is maintained strategically within the socket as the user walks. Under this approach, vacuum is maintained as the patient ambulates with the artificial limb.

This method of evacuating a prosthetic socket has several disadvantages, however. First, the weight activated pump is heavy, and cannot be removed even in the case of a pump failure. The weight activated pump also requires a certain minimum space between the users limb and prosthetic foot, which may be more than is available if the patient has a relatively long residual limb. This prohibits the use of this technology for many artificial limb users. Further, a weight-activated pump system requires some number of weight activated strokes before becoming effective.

Another evacuation method disclosed in the above-referenced patent uses a hand-held sub-atmospheric pressure pump, much like that used to bleed brake systems on an automobile. This method provides for acceptable socket evacuation, but requires the individual to carry the hand-held pump upon their person for use in case of vacuum failure. The hand-held pump is also awkward for many individuals to use and requires a certain amount of dexterity and strength to operate. This is a common problem for elderly individuals.

As can be understood from the foregoing discussion, known mechanical systems for evacuating a prosthetic socket have several disadvantages. Aside from those specific disadvantages detailed above, such mechanical systems are further burdened with other general problems. Primarily, the evacuation pump associated with such systems is active only when the user is ambulating, and then is activated with every step—regardless of the wishes of the user.

Therefore, one general disadvantage to such a mechanical systems is that the pump is unable to draw vacuum when the user is sedentary. This means that absent the carrying and use of a separate hand-held pump, there is no way to properly don an associated prosthesis without standing up and walking on the prosthesis in a partially donned (i.e., non-evacuated) state. Similarly, if the socket loses pressure while the user is sitting or otherwise non-ambulatory, there is no way (aside from a separate hand-held pump) to re-evacuate the socket other than walking or bouncing on the now improperly suspended prosthesis.

Another disadvantage to such mechanical evacuation systems is that a weight-activated pump will always eventually evacuate the prosthetic socket to some predetermined level. As such, there is no way for a user to adjust the level of vacuum to coincide with a particular activity or comfort level. For example, a user would not be able to increase the vacuum level over some typical vacuum level during a period of increased activity, nor decrease the vacuum level to compensate for a particularly sore or sensitive residual limb.

Yet another disadvantage to known evacuation systems is that they tend to be bulky, unattractive, and difficult to cosmetically finish. For example, it may be difficult or impossible to apply a cosmetic cover that imparts a lifelike appearance to a prosthesis because the evacuation device may be too bulky. Also, applying a cosmetic cover may interfere with the function of the evacuation system or may prevent or discourage recommended access to the evacuation system.

Thus, there is a need for improved means of achieving sub-atmospheric pressure within a prosthetic socket. The present invention satisfies this need.

SUMMARY OF THE INVENTION

The present invention overcomes the disadvantages inherent to known prosthetic socket evacuation devices using mechanical (e.g., weight-activated) pumps. Rather, the present invention is directed to socket evacuation device employing an electrically-activated pump. Because the electrically-activated pump does not require manual manipulation to create vacuum, it is substantially easier to use than a manual pump. Further, due to the compact size and minimal power consumption associated with an evacuation device of the present invention, it may be readily incorporated into/onto a prosthesis.

A device of the present invention thus affords substantial general advantages over the manual pumps and gait-driven pumps of the prior art, and the inventors are believed to be the first to present a practical approach to providing an electrically evacuated prosthetic device. The '868 patent referenced above suggests the inclusion of a generically drawn "vacuum source" and "power source", and a regulator for automatic vacuum maintenance, into an outer socket of a prosthesis (see, e.g., FIGS. 7 and 9 and discuss thereof); however, there is no specific reference therein to a vacuum source or power source that is of suitable size and weight for such an application, as is provided by the inventors hereof. The present invention thus represents an advance and an enabled approach to providing an electrically actuated, portable vacuum pump in a prosthesis.

An electrically-activated evacuation device of the present invention offers additional advantages not possible with a manual or gait-driven device. For example, in addition to embodiments wherein the vacuum level is directly controlled by the user, the present invention may also possess semi-automatic or automatic vacuum level control and/or semi-automatic or automatic vacuum regulation.

Yet another advantage of an electrically-activated evacuation device of the present invention is that it can be made to blend in with the rest of a prosthesis, and can actually be integrated into the prosthesis—making it much easier to cosmetically finish the prosthesis, if so desired. Even in an embodiment using wireless capabilities, applying a cosmetic cover will not interfere with the function of the evacuation system.

The above and other objects and advantages of the present invention shall be made apparent from the accompanying drawings and the description thereof.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIGS. 22a-22b are schematic diagrams illustrating one useable embodiment of a electronic vacuum control system that includes a handheld controller wirelessly connected to a vacuum control assembly.

DETAILED DESCRIPTION OF THE EXEMPLARY EMBODIMENT(S)

Figure 1:
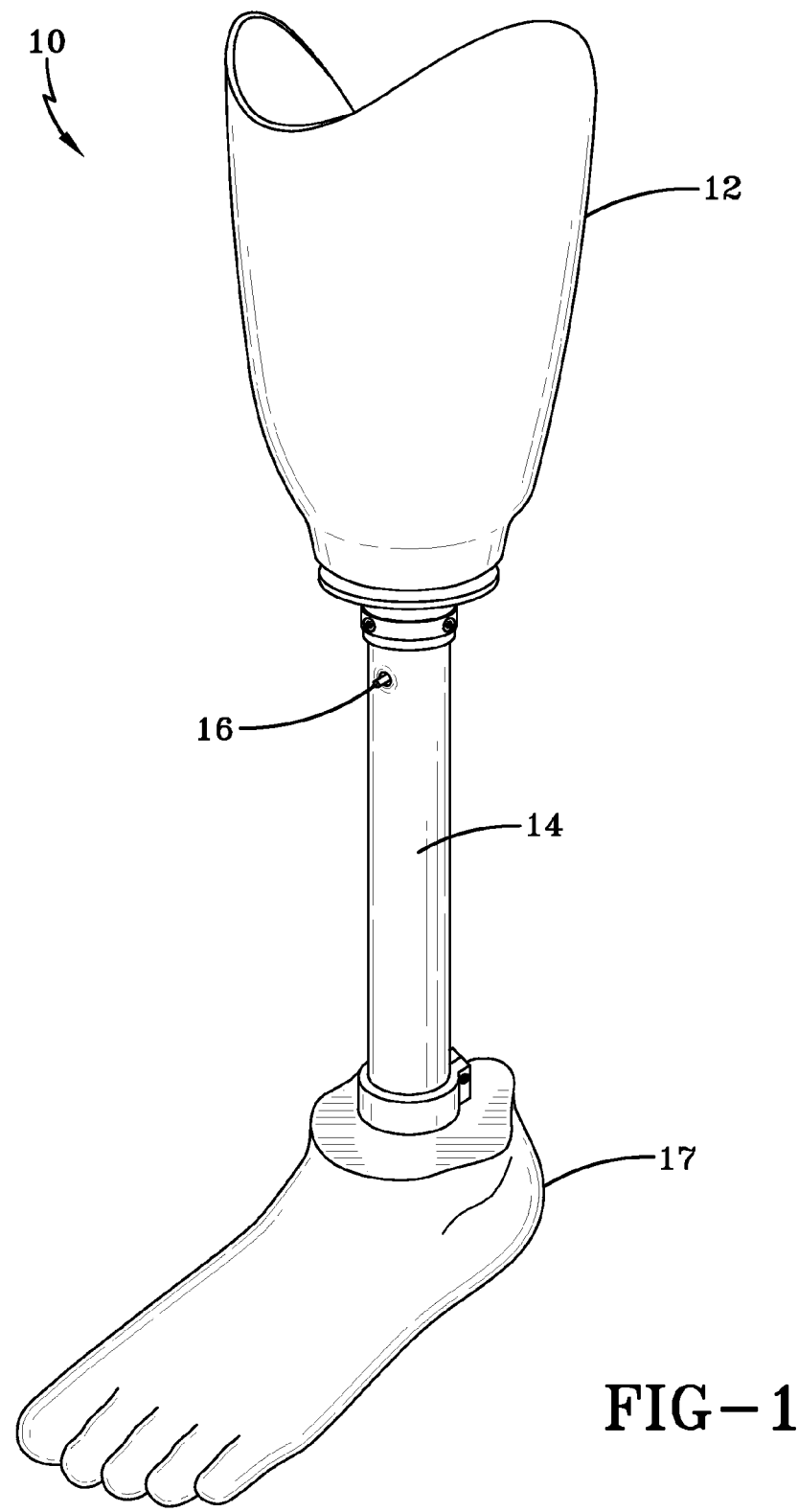
FIG. 1 illustrates a prosthetic limb incorporating an electric vacuum pump according to one embodiment of the present invention.

FIG. 1 illustrates one embodiment of a prosthesis 10 in accordance with principles of the present invention. The prosthesis includes a socket 12 for receiving an amputee's residual limb, a column (pylon) 14, which is typically a cylindrical section of lightweight metal such as aluminum, and an artificial foot 17. As can be seen in FIG. 1, the pylon 14 includes a vacuum actuator button 16 used to actuate an electric vacuum pump within the pylon that draws air from the socket 12 and, as a result, draws the residual limb into intimate contact with the interior of the socket 12.

Figure 2:
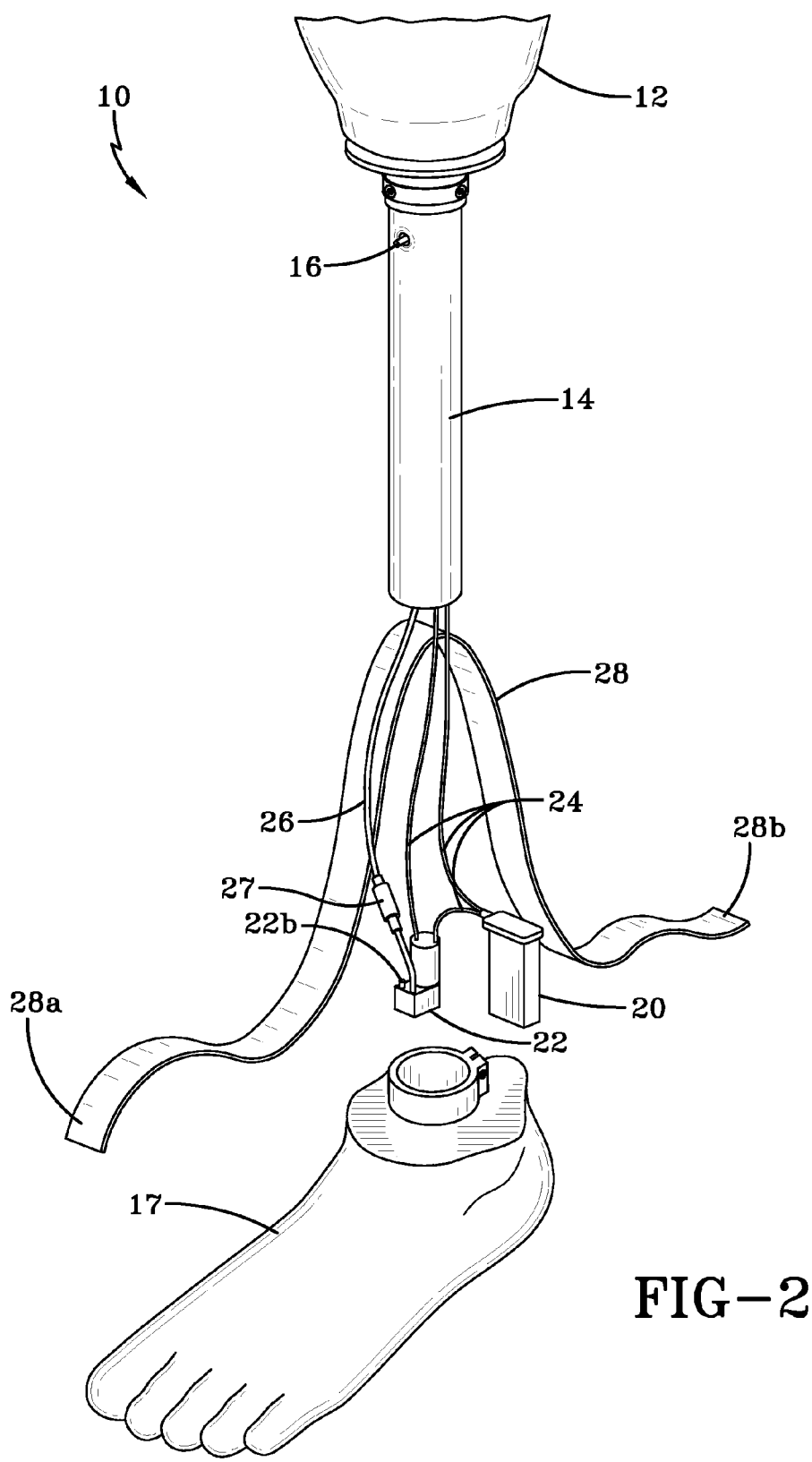
FIG. 2 is a disassembled view of the prosthetic limb of FIG. 1, illustrating internal components thereof.

FIG. 2 illustrates the prosthesis of FIG. 1 in a disassembled state to show the component parts within the pylon 14. Internal to the pylon 14 is a power source 20, such as a capacitor or a conventional 9-volt battery, a vacuum pump 22, and electrical lines 24 for delivering electrical power from power source 20 to vacuum pump 22, and vacuum line 26 for drawing vacuum from socket 12 through a check valve 27. The power source 20, vacuum pump 22, electrical lines 24, vacuum line 26 and check valve 27 components are inserted into the pylon 14 after insertion of a ribbon 28, so that the ribbon 28 may be subsequently used to extract the components (e.g., for changing or recharging the power source 20).

One suitable type of vacuum pump for use in the present invention is the model VMP 1624 Series of vacuum pumps, available from Virtual Industries, Inc., 2130 Vector Place, Colorado Springs Colo. A specific model that has been found to be particularly suitable for application as shown herein is model 1624-009-S. This family of pumps is capable of drawing vacuum up to 18 inches of mercury (−594 millibar), which is sufficient for use in a prosthesis. The pump flow rate is as large as 1300 ml per minute. The voltage for the specific model identified above is 9 volts, permitting use of the pump with a conventional disposable or rechargeable 9-volt battery. A rechargeable 8 volt lithium ion polymer battery (model LIPBA-300-8, rated at 300 mAh/8 v) available from OPRA-TECH Engineering in Warren, Ohio may also be used.

Another line of pumps suitable for use in any embodiment of the present invention are available from the Oken Seiko Co., Ltd. in Tokyo, Japan. One particular pump model that has shown itself acceptable in this regard is model S02R6331, which can operate on between 1.5-3.0 volts. Consequently, such a pump may be powered by a small capacitor, 1-2, 1.5 v AAA disposable or rechargeable batteries, or any other acceptable standard batteries.

Yet another type of vacuum pumps suitable for use in any embodiment of the present invention are those similar to the model SA0002005 manufactured by Dynaflo of Birdsboro, Pa. With the appropriate electronics and controls, these pumps have been found to work well and may be adequately powered by a single lithium ion battery. While several acceptable batteries may be used for this purpose, the LP561943A lithium ion battery manufactured by Sanyo GS has been found to be particularly useful due to its small size and reliability. When using a lithium ion battery it is preferable to incorporate a safety circuit to protect both the user and the battery from the potential effects of battery misuse. One such suitable safety circuit is the G7070 protection circuit module made by Nexcon Technology Company of Korea. The G7070 module is small in size and offers a comprehensive array of protection functions.

Most pumps of appropriate size and power for use in an embodiment of the present invention are of a design that includes a diaphragm made of Ethylene Propylene Diene Monomer (EPDM) rubber. EPDM is commonly used as a diaphragm material because of its superior performance under a variety of conditions for long periods of time. Unfortunately, in the present invention the pump, including its diaphragm, is exposed to a variety of substances that can adversely affect the material properties of the diaphragm. This can result in premature failure, or otherwise adversely affect the performance of the pump. Some of the substances that can adversely affect an EPDM pump diaphragm include perspiration, exudate from a prosthetic liner (especially mineral oil), lubricants, and cleaning substances.

Certain elastomers, which are not commonly used in pump diaphragms, have been found to perform better under such conditions than EPDM. These elastomers include, for example: silicone, fluorocarbon elastomers, florosilicones, neoprene, and Hydrogenated Nitrile Butadiene Rubber (HNBR). While these elastomers might not provide the same level of long term performance as EPDM in applications in which such pumps are normally used, they do, however, provide a significant improvement in useful life with respect to the conditions relevant to the present invention. Therefore, these alternative elastomers could also replace other components of a vacuum system that are commonly made of EPDM, such as a check valve, and which could be exposed to the same or similar substances as the diaphragm.

Figure 5:
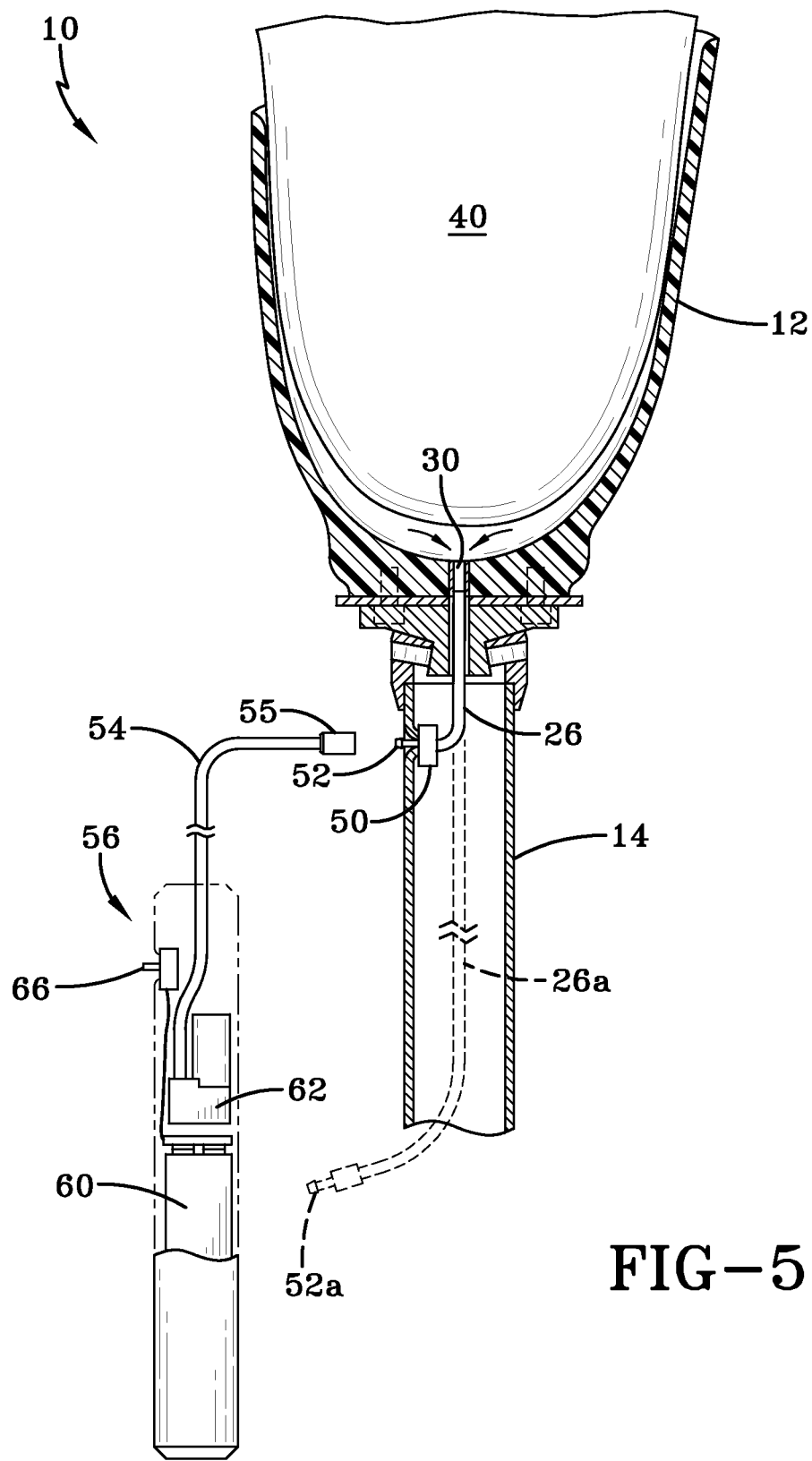
FIG. 5 illustrates another embodiment of the present invention, in which the electric pump and power source are housed in a separate portable evacuation device.

Therefore, it can be seen that electrically-powered vacuum pumps are available having a size and weight that permits their installation on or within the pylon 14, a housing, or another component of a prosthesis without substantially increasing the effort and drain on the patient using the prosthesis. Similarly, such pumps can be easily incorporated into a portable inflation pump such as is illustrated in FIG. 5 below.

Figure 3:
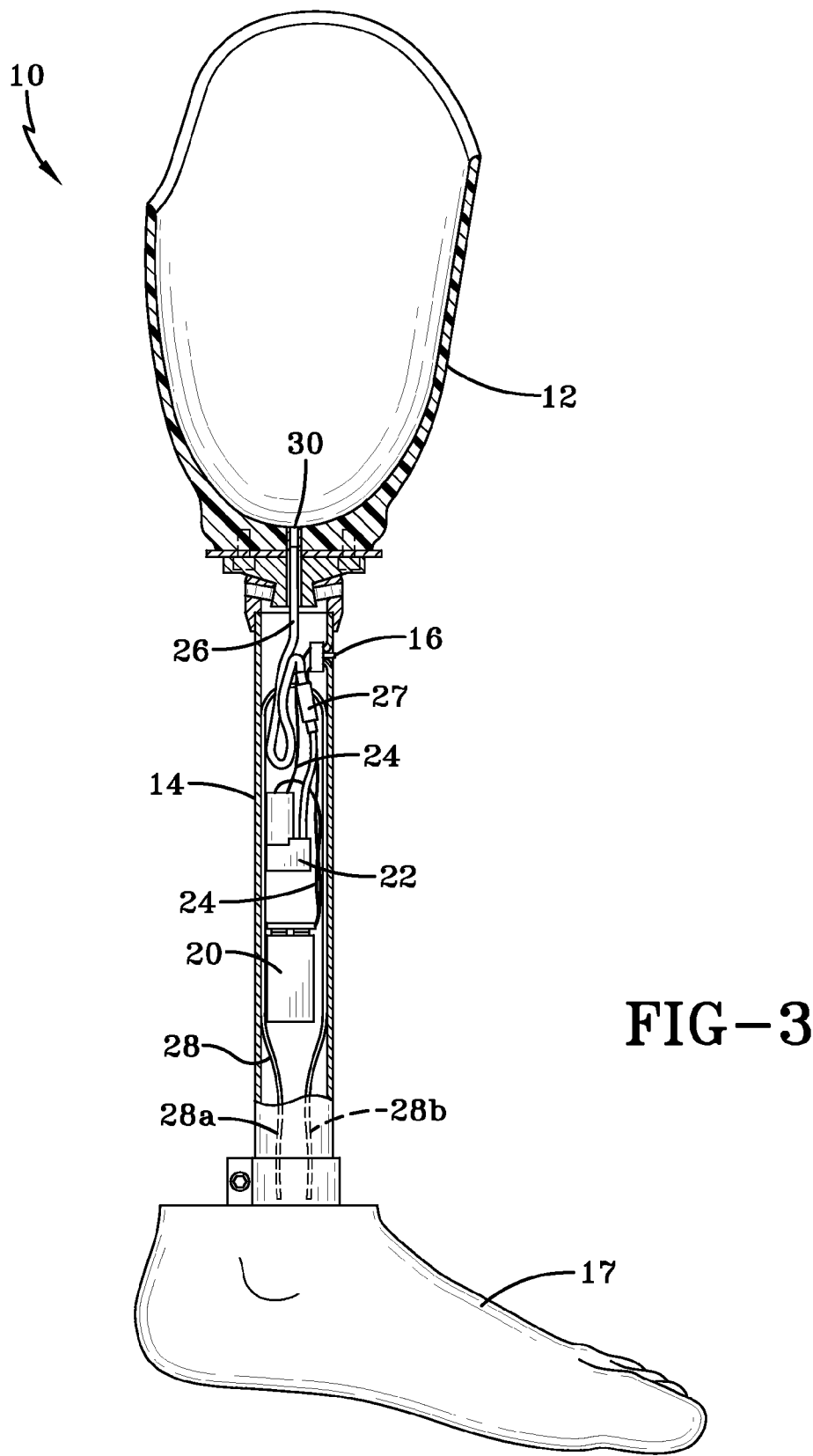
FIG. 3 is a cutaway view of the prosthetic limb of FIG. 1 showing the internal components as positioned when the limb is in use.

FIG. 3 is a cross-sectional view of the prosthetic device 10 illustrating the components of FIG. 2 after insertion into the pylon 14. As can be seen in FIG. 3, the ribbon 28 forms a loop surrounding the power source 20 and the vacuum pump 22 so that those components may be withdrawn from the pylon 14 by pulling at the ends 28a and 28b of ribbon which extend to the bottom end of pylon. FIG. 3 further illustrates the vacuum and electrical circuits formed by the various components of the prosthetic device 10. Specifically, an electrical circuit is formed by the electrical connections 24, the positive and negative contacts of the power source 20 and the positive and negative terminals of vacuum pump 22. As can be seen, one electrical connection directly connects one terminal of the power source 20 to one terminal of vacuum pump 22, while further electrical connections connect the other terminal of the power source to the other terminal of vacuum pump via electrical switch 16. Thus, by closing electrical switch 16, electrical power is supplied to the vacuum pump 22, causing the vacuum pump to operate and evacuate the socket 12.

A user of a prosthetic device as thus described can readily create elevated vacuum to any level desired, at least to the limits of vacuum that can be drawn by the vacuum pump 22. No particular vacuum level is required or contemplated by this particular embodiment of the present invention, as individual patients may have specific preferences and physical and/or physiological needs that dictate the level of vacuum drawn. The described exemplary vacuum pumps each have a flow rate sufficient to evacuate a typical socket to the desired vacuum level within about 30 seconds of vacuum pump operation. Some users will require very little vacuum within the socket 12, whereas others will desire a higher level of vacuum and may, therefore, operate the vacuum pump for a longer period of time. For example, certain levels of vacuum may be desirable due to their potential to reduce the risk of ulceration and improve vascular flow. Furthermore, the amputee may readily re-apply vacuum using the pump as described above as needed.

As can be further seen in FIG. 3, the vacuum line 26 connects the vacuum pump 22 to a vacuum orifice 30 located in the socket 12 so that the socket may be evacuated by operation of the vacuum pump. As seen in FIG. 2, air drawn through the vacuum line 26 in this embodiment of the present invention is expelled via an outlet port 22b on vacuum pump 22 into the interior of the pylon 14. Air expelled into the pylon 14 is vented to the atmosphere, as the interior of a typical pylon is not generally sealed from the atmosphere.

As can be seen in FIG. 2 and in FIG. 3, the vacuum line 26 includes a check valve 27 for permitting airflow through the vacuum tube 26 to the vacuum pump 22 but preventing reverse airflow from the vacuum pump through the vacuum tube and into the socket 12. The check-valve 27 may be a duckbill-valve or another known type of one-way valve.

Figure 4A:
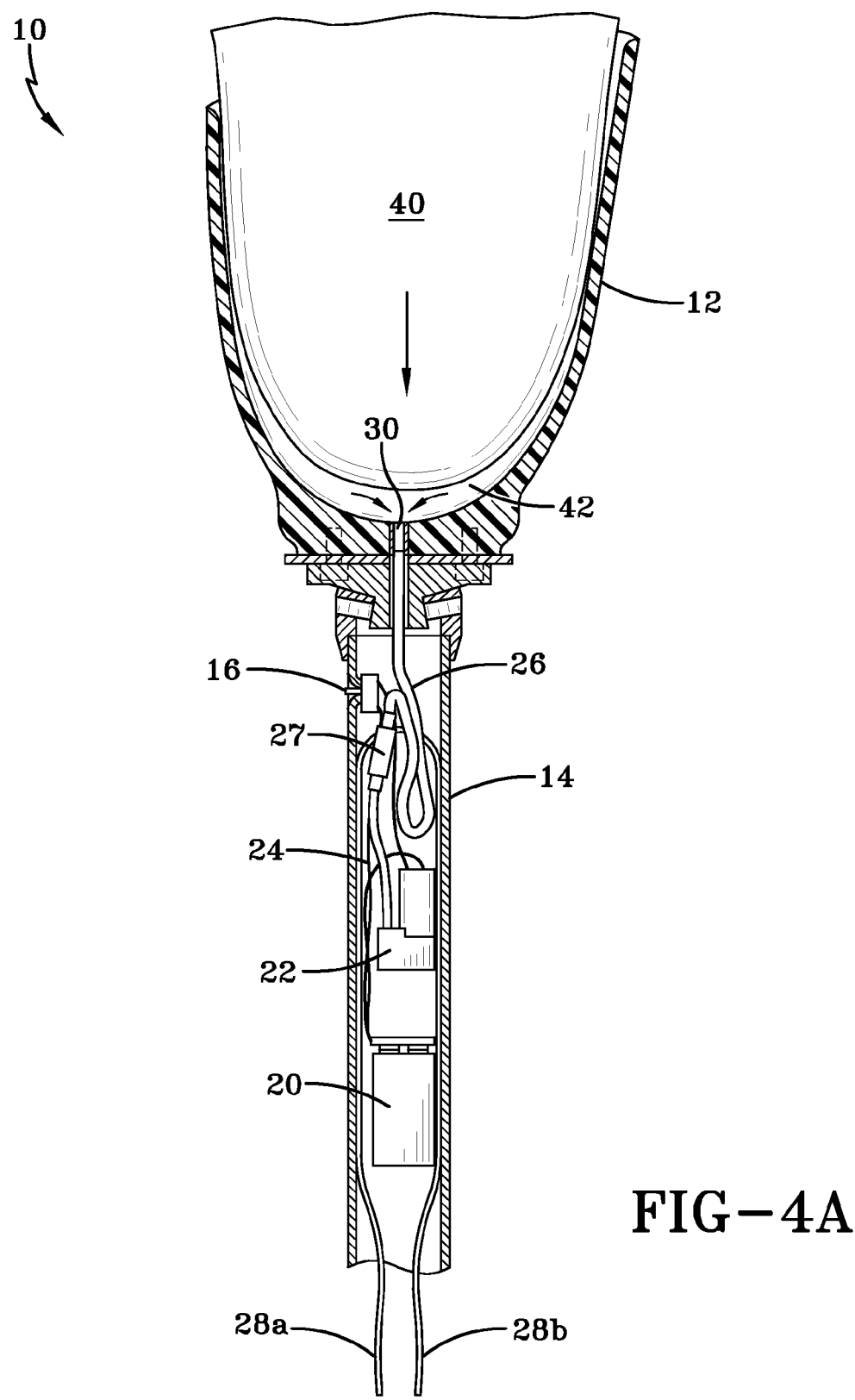
FIGS. 4A and 4B are cutaway views of the prosthetic limb of FIG. 1 showing its use in creating vacuum engagement of a limb with a socket.

Referring now to FIG. 4A, use of the inventive prosthetic device 10 in connection with a patient's residual limb is illustrated in further detail. As seen in FIG. 4A, a patient's residual limb 40, typically having a liner donned thereon, is inserted into the socket 12, commonly leaving a cavity 42 filled with air. In an application wherein a liner without an outer fabric covering is used, an air wick sheath such as a fabric can be used to prevent the urethane, silicone, or thermoplastic liner from sealing the vacuum orifice and thus limiting the vacuum to the opening of the orifice only. Use of an air wick sheath over such a liner can allow air to be evacuated over a larger area of the residual limb. In applications wherein a fabric covered liner, such as one of the Alpha® family of liners available from The Ohio Willow Wood Company in Mt. Sterling, Ohio is used, the use of an air wick sheath is unnecessary.

Figure 4B:
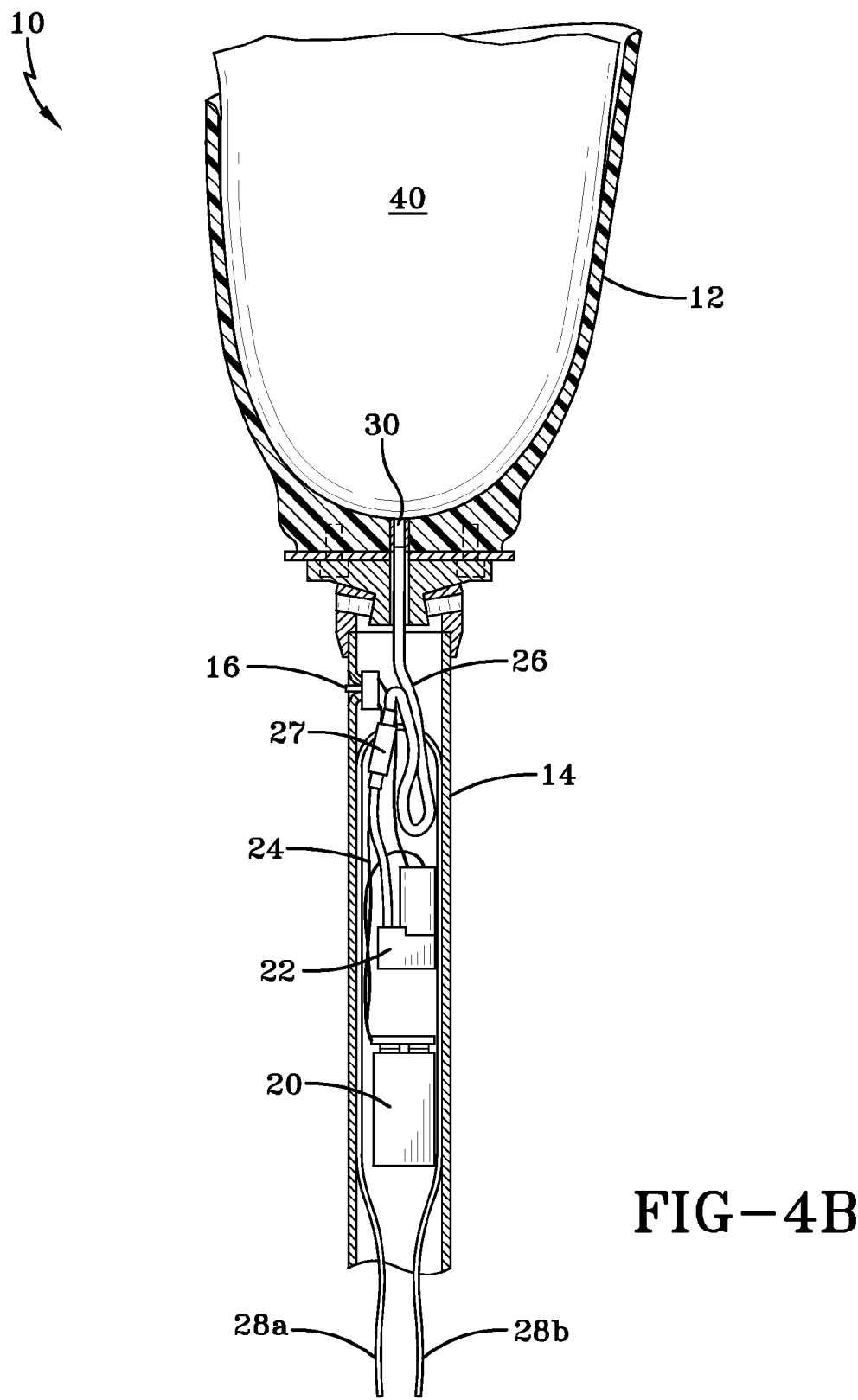

With the liner-covered residual limb inserted into the socket 12, the patient depresses the actuator button 16, activating the vacuum pump 22 and causing air from the cavity 42 to be drawn through the vacuum tube 26 and the check valve 27 to the vacuum pump 22, whereafter the air is expelled into the interior of the pylon 14. The resulting vacuum in the cavity 42 draws the residual limb 40 into tight coupling with the interior of the socket 12, and permits use of the prosthetic device 10 for various ambulatory activities. The vacuum induced coupling between the residual limb 40 and the interior of the socket 12 can be best observed in FIG. 4B.

Referring now to FIG. 5, an alternative embodiment of the present invention is described. In this alternative embodiment, the pylon 14 is simplified by not including therein the vacuum pump 22 or the power source 20. Rather, the pylon 14 contains only the vacuum line 26 that is coupled to the interior of the socket 12. The vacuum line 26 connects to a vacuum orifice coupler 50/52, which includes two parts. A first part of the coupler 50/52 is a check valve 50 that permits airflow from the socket 12 through the vacuum line 26, but blocks reverse airflow from the exterior environment into the vacuum line and socket. As shown, the coupler 50/52 may also include an orifice 52 for receiving a vacuum line from an external portable vacuum pump 56.

A portable evacuation device 56 includes its own vacuum line 54 with a coupler 55 on the end thereof for connection to the vacuum orifice coupler 52. The interior of the portable evacuation device 56 includes a power source 60, such as a capacitor or battery, a vacuum pump 62, and a control switch 66. The power source 60 is electrically connected to the vacuum pump 62 via electrical connections similar or identical to those described above with reference to FIGS. 2-4B, and the vacuum line 54 is connected to the inlet port of the vacuum pump 62. The portable evacuation device can thus be used to draw air from the socket 12 by connecting the coupler 55 to the coupler 52, then actuating switch 66 to activate vacuum pump 62 and draw the air through the vacuum line 54.

One advantage of a portable evacuation device as shown in FIG. 5 is that the weight of the power source 60 and the vacuum pump 62, although minimal, is removed from the prosthesis. Also, a patient with a relatively long residual limb and, therefore, a short pylon 14, may not have sufficient volume in the pylon to enclose the motor and/or power source therein as shown in the preceding drawings. Similarly, above-knee amputees may not have enough room to incorporate a vacuum system between a prosthetic knee coupler and the end of the users socket. In such cases, a portable evacuation device may be utilized to provide a portable vacuum source for the amputee.

Figure 6:
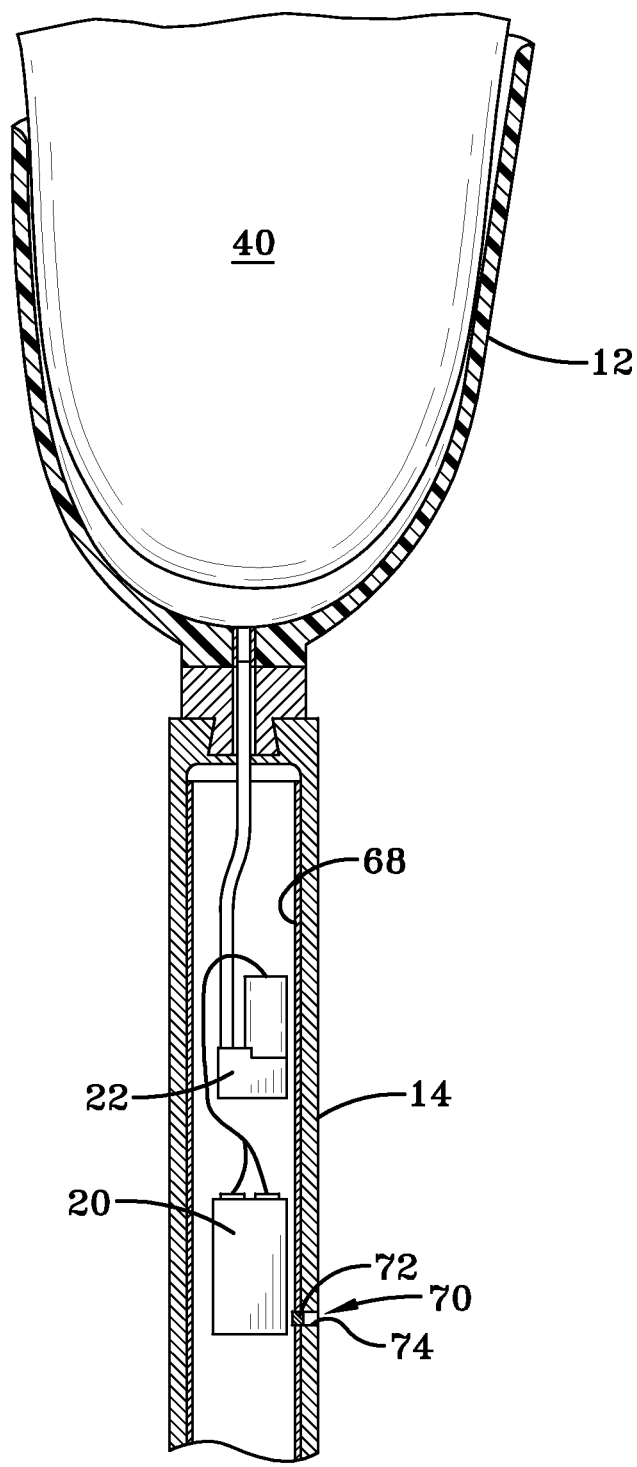
FIG. 6 depicts another embodiment of the present invention, wherein the electric pump and power source are placed into a sleeve that is subsequently installed into a pylon.
Figure 7:
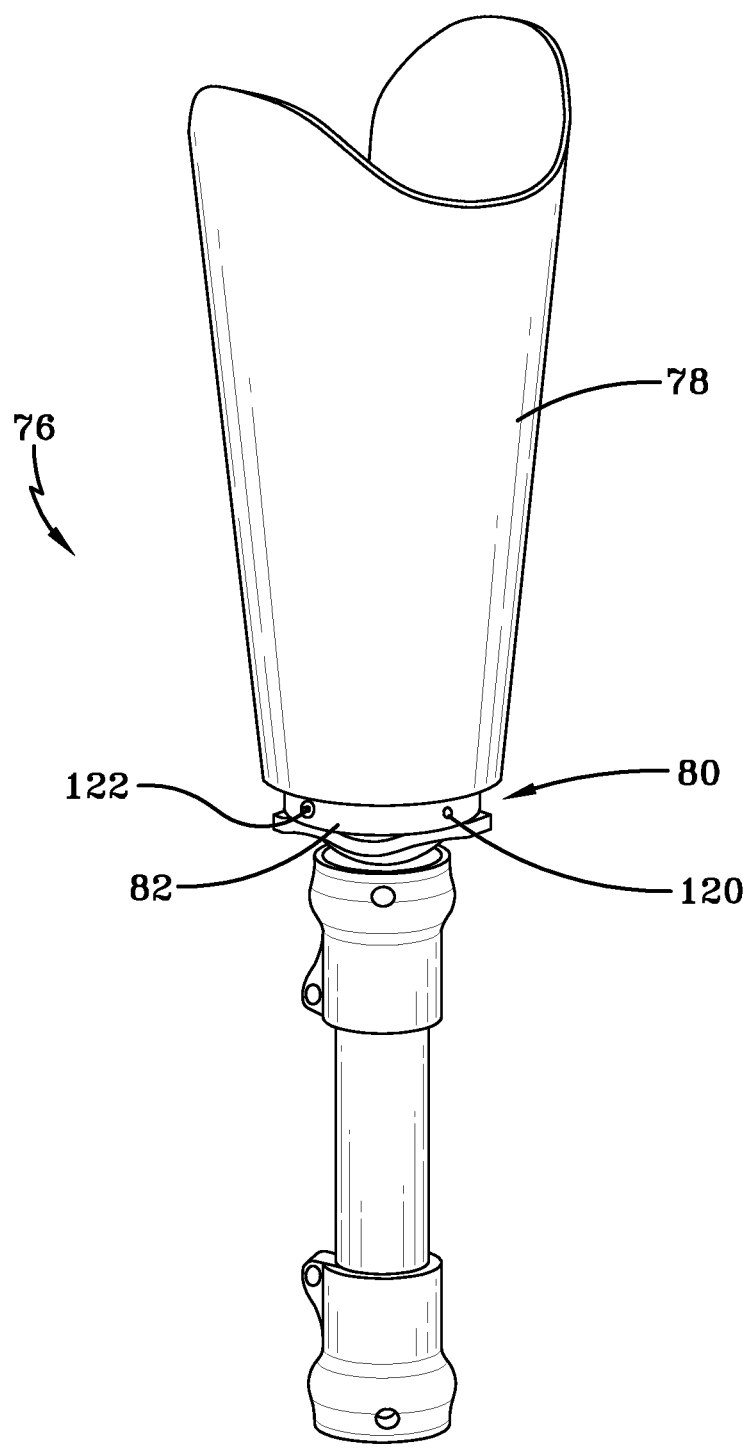
FIG. 7 illustrates a prosthetic limb employing another embodiment of the present invention, wherein an evacuation device includes a vacuum pump and power source that are located within a housing designed for attachment to a universal distal adapter that is built into the distal end of a prosthetic socket.
Figure 8:
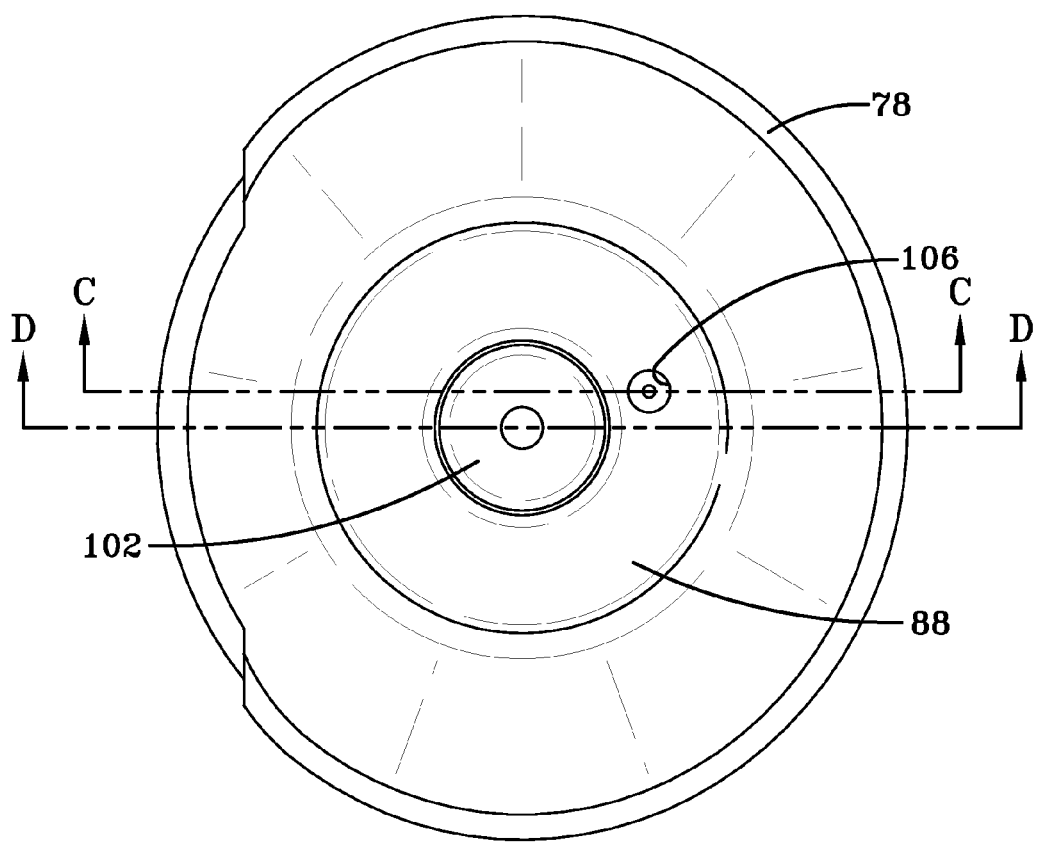
FIG. 8 is a plan view into the socket of the prosthetic limb of FIG. 7, wherein a portion of the universal distal adapter and a portion of the housing are visible.
Figure 9:
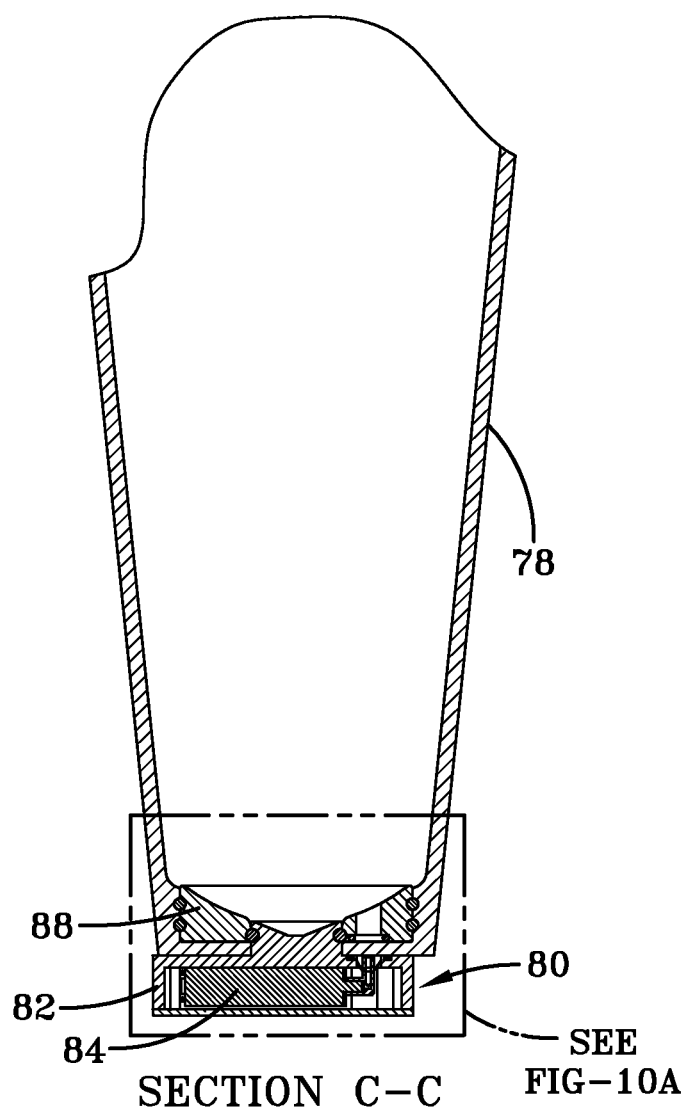
FIG. 9 is a section view of a portion of the prosthetic limb of FIG. 7, taken along line C-C of FIG. 8.
Figure 10:
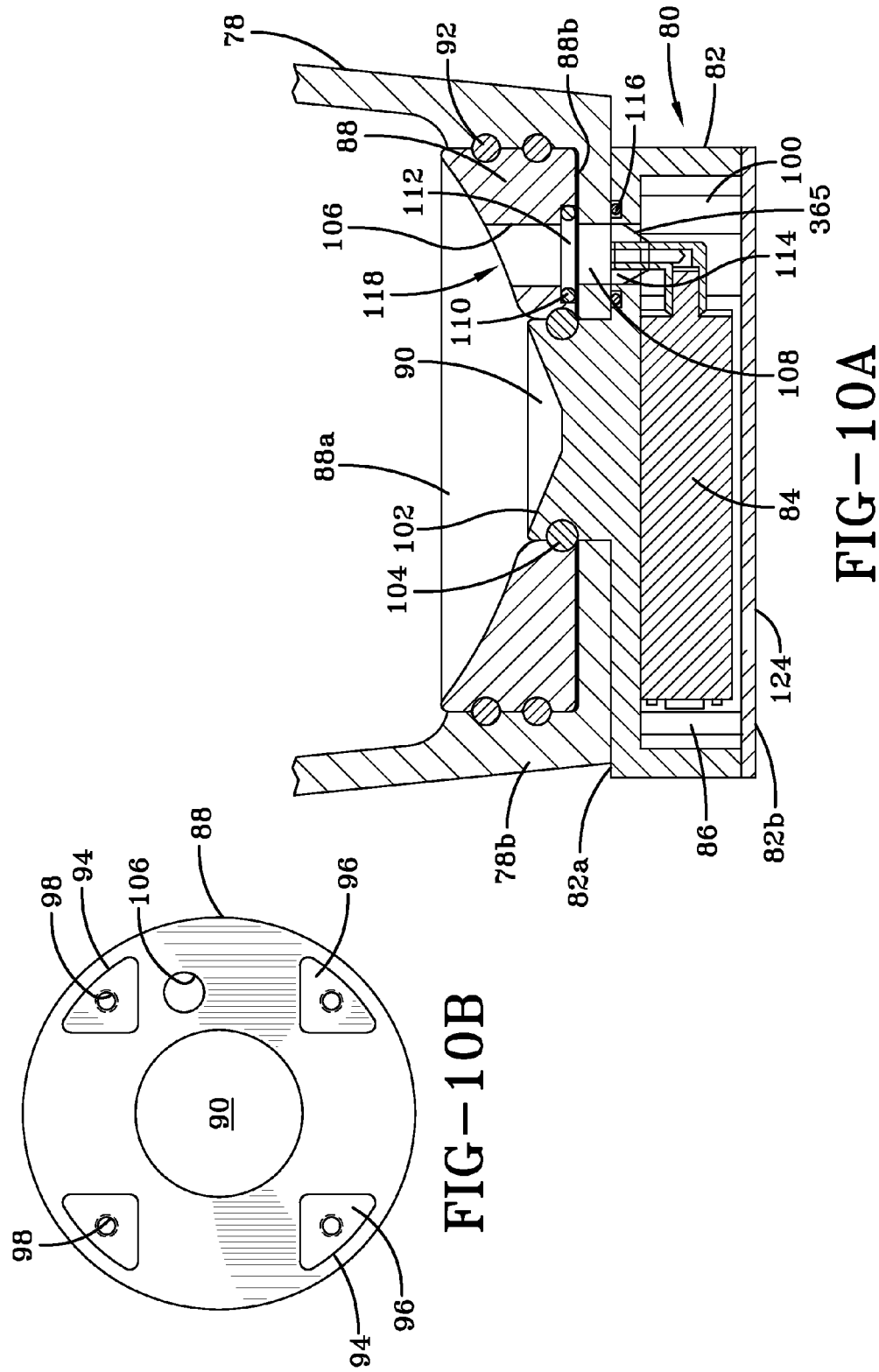
FIG. 10A is an enlarged view of the detailed area called out in FIG. 9.
FIG. 10B is a bottom plan view of the universal distal adapter.
Figure 11:
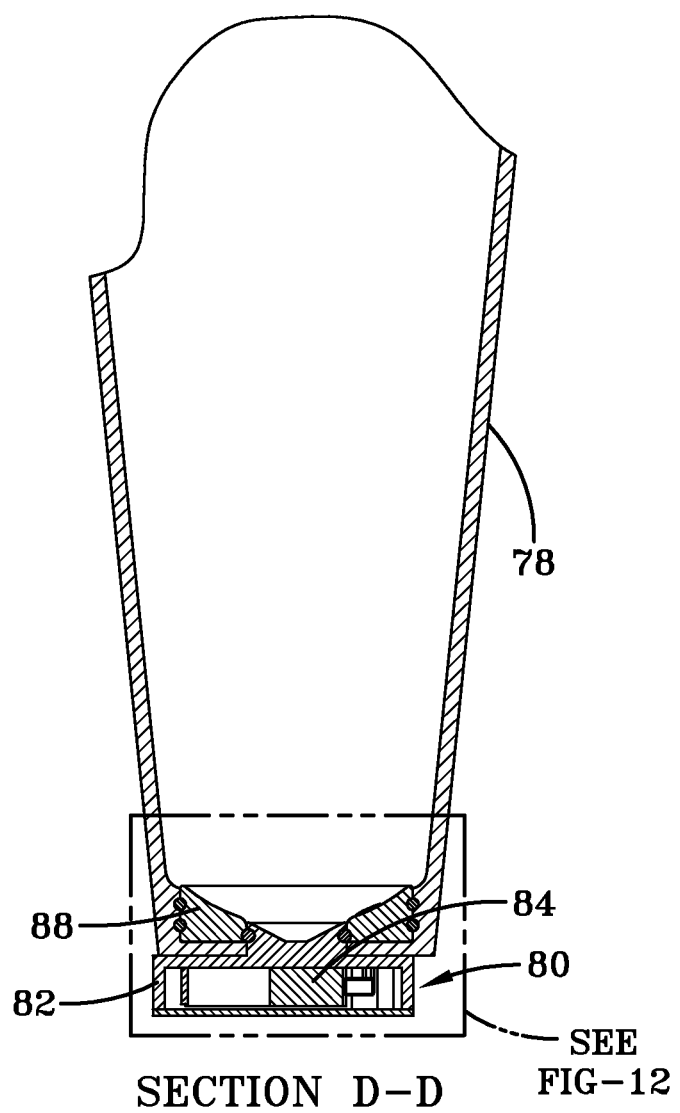
FIG. 11 is a section view of a portion of the prosthetic limb of FIG. 7, taken along line D-D of FIG. 8.
Figure 12:
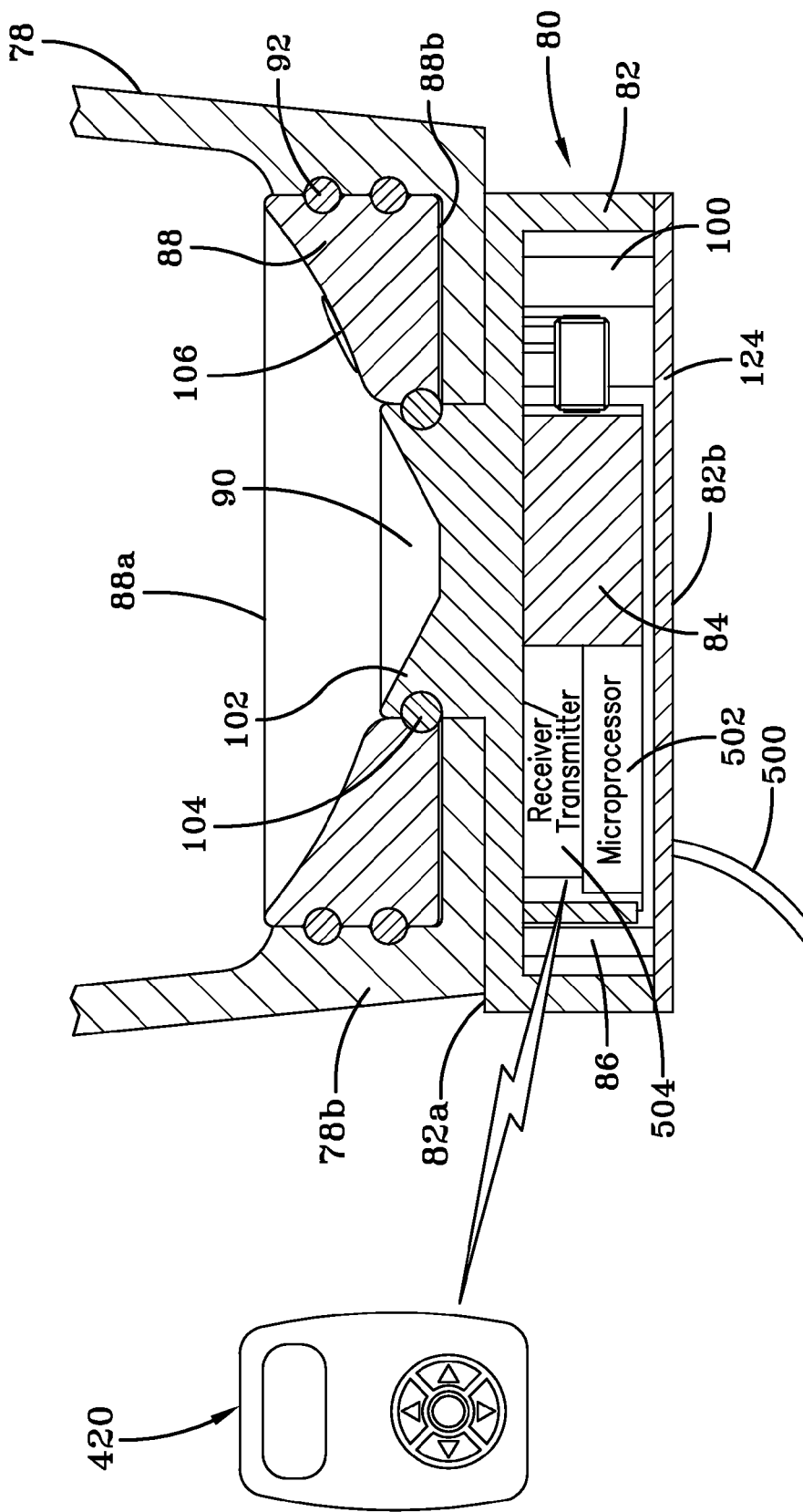
FIG. 12 is an enlarged view of the detailed area called out in FIG. 11.

Another embodiment of the present invention is illustrated in FIG. 6. In this embodiment, a vacuum pump and power source are again installed to a pylon. The vacuum pump, power source and pylon may be the vacuum pump 22, power source 20 and pylon 14 shown in FIGS. 2-4B, for example, or may be entirely different components.

Unlike the installation shown in FIGS. 2-4B, this embodiment of the present invention makes use of a special sleeve 68 into which the vacuum pump 22 and power source 20 are installed prior to insertion into the pylon 14. Preferably, the sleeve 68 is formed from a thin and lightweight material that may substantially conform to the shape of the pylon interior. As shown, the sleeve 68 consists of a thin plastic tube, although the use of other materials is certainly also possible. One or both ends of the sleeve 68 may be open, or the end(s) may be closed but for small access openings required for vacuum lines or electrical wiring.

The vacuum pump 22 and power source 20 may be retained within the sleeve 68 simply by a tight fit between the components and the interior of the sleeve. In an alternate embodiment of the sleeve (not shown), the sleeve interior may be provided with a special geometry designed to mate with and retain the vacuum pump 22 and/or power source 20.

With the vacuum pump 22 and power source 20 installed in the sleeve 68, the housing is inserted into the pylon as shown in FIG. 6. Retention of the sleeve 68 within the pylon 14 can be achieved by a tight fit between the sleeve and the pylon interior or, preferably, a retention means may be provided. Such a retention means may take many forms such as, for example, a pin, fastener, tab or other retainer that releasably affixes the sleeve 68 to the pylon 14. Various types of releasable adhesive, such as one or more pieces of double-stick tape or Velcro® may also be used for this purpose. As shown in FIG. 6, however, retention of the sleeve 68 is accomplished by means of a detent 70. More specifically, when the sleeve 68 is properly inserted into the pylon 14, a projection 72 located on the exterior of the housing engages a hole or aperture 74 provided in the wall of the pylon. The interaction between the projection 72 and the aperture 74 is sufficient to retain the sleeve 68 during normal use of an associated prosthesis, while also allowing for disengagement and deliberate removal of the sleeve if desired. The sleeve 68 may be used in any embodiment of the present invention wherein a vacuum pump and power source are installed within a pylon or other hollow prosthetic component.

Another embodiment of the present invention is shown in FIGS. 7-12. In this embodiment, a prosthetic limb 76 includes an evacuation device 80 having at least a vacuum pump 84 and power source 86 located in a housing 82 that is specially designed to mate with a universal distal adapter 88 that is affixed to or integrated into a prosthetic socket 78. Such a distal adapter 88 is shown to be substantially located in the distal end of the prosthetic socket 78 in FIGS. 8-12, and may employ the four-hole attachment pattern common to the prosthetics industry.

A proximal (mounting) face 88a of the distal adapter 88 that resides interior to the socket 78 is preferably, but not necessarily, concave, to better receive the distal end of the residual limb. The distal adapter 88 also has an aperture 90 passing axially therethrough. The aperture 90 allows for the passage of various suspension components such as, for example, locking pins and lanyards, and also receives a portion of the evacuation device housing 82 when the evacuation device 80 is used. Suspension devices associated with such suspension components can be designed to mate with the distal adapter 88 in the same manner as the evacuation device 80, and theses devices may be made to be interchangeable.

At least in the embodiment shown, wherein a suction seal is desired, the distal adapter 88 is optionally, but not necessarily, equipped with one or more o-rings 92 or similar sealing elements that traverse its periphery and assist with providing an air-tight seal between the outer surface of the distal adapter 88 and the interior of the socket 78. Other sealing means may also be employed.

As can be best observed in FIG. 10B, a number of mounting projections 94, each having a flat mounting surface 96, extend downward from a bottom (connecting) face 88b of this distal adapter 88 and are exposed along the bottom of the distal end 78b of the socket 78. This can be achieved during lamination of the socket 78 by employing a temporary cover plate to protect the mounting surfaces 96 and the aperture 90, while simultaneously allowing socket material to fill the channels formed between the mounting projections 94. The end result of this technique is a substantially flat mounting area at the distal end 78b of the socket 78, with an aperture that connects the interior of the socket to the atmosphere via the aperture 90 in the distal adapter 88. In other embodiments, a distal adapter having a single uniform mounting surface that is exposed along the distal end 78b of the socket 78 may alternatively be used in place of an adapter having mounting projections. It should be noted that any of such embodiments of the distal adapter can also be used with thermoplastic sockets to create either diagnostic or definitive sockets. This particular distal adapter 88 is especially useful in this manner since it can be used in a thermoplastic diagnostic socket as well as a definitive socket—whether the definitive socket is laminated or thermoplastic.

In this particular embodiment, each mounting surface 96 has a threaded mounting hole 98 for receiving a like-threaded fastener. The mounting surfaces 96 mate with the proximal (mounting) side 82a of the evacuation device housing 82 when the evacuation device 80 is affixed to the distal end of the socket 78. As shown, the housing 82 has a number of thru-holes 100 that are arranged to align with the mounting holes 98 located in the mounting surfaces 96 of the distal adapter 88. Fasteners may be passed through the thru-holes 100 in the housing 82 and threaded into the distal adapter mounting holes 98 to secure the evacuation device 80 to the distal end of the socket 78.

Various prosthetic components may be affixed to the distal (connecting) side 82b of the evacuation device housing 82 by the same fasteners. These prosthetic components may include, for example, pyramid adapters, Symes adapters, prosthetic ankles, prosthetic feet, prosthetic knees, and other components forming the remainder of a prosthesis.

In the embodiment shown, a sealing extension 102 projects upward from the mounting face 82a of the evacuation device housing 82 through the aperture 90 in the distal end 78b of the socket 78 and into the aperture 90 in the distal adapter 88. The sealing extension 102 preferably carries an o-ring 104 that acts to seal the aperture 90 in the distal adapter 88.

With the above-described construction, the distal end 78b of the socket 78 is made air tight. As such, mating vacuum passages 106, 108 extend through the distal adapter 88 and the distal end 78b of the socket 78. The vacuum passage 108 in the socket 78 may be created during lamination by means of a projection on the cover plate used to expose the mounting faces 96 of the mounting projections 94. Alternatively, the vacuum passage 108 may be bored through the distal end 78b of the socket 78 after lamination thereof. The interface of the vacuum passages 106, 108 may be further sealed with an o-ring 110 if desired. Such an o-ring 110 may be installed into a recess or counterbore 112 in the distal adapter 88.

In this particular embodiment, an evacuation device vacuum passage 114 extends from the vacuum pump 84 through the mounting surface 82a of the evacuation device housing 82. The evacuation device vacuum passage 114 is aligned and mates with the vacuum passages 108, 106 in the socket 108 and distal adapter 106 when the evacuation device 80 is properly mounted to the distal end 78b of the socket 78. An o-ring 116 or similar sealing element may be located in the mounting face 82a of the evacuation device housing 82 and around the evacuation device vacuum passage 114 to ensure a good seal. The connected vacuum passages 106, 108, 114 essentially form one continuous vacuum passageway 118 that allows the vacuum pump 84 of the evacuation device 80 to evacuate air from the interior of the socket 78. A one way valve may be placed in any of the vacuum passages 106, 108, 114 to ensure that air cannot flow into the socket 78.

Air evacuated from the socket may be discharged by the vacuum pump 84 through an exhaust port 120. The exhaust port 120 may reside at various locations in the housing 82. The evacuated air may be discharged directly to the atmosphere, or into another prosthetic component, such as a pylon, where it can thereafter leak to the atmosphere. A one-way valve and/or muffler can be associated with the exhaust port 120.

In an alternate, but similar embodiment of the present invention, an evacuation device vacuum passage may pass from a vacuum pump through the sealing extension 102— instead of through the mounting face 82a of the housing 82. In this case, communication with the socket interior occurs through the aperture 90 in the distal adapter 88 and, therefore, the distal adapter vacuum passage 106 and socket vacuum passage 108 can be eliminated or plugged.

In this embodiment of the evacuation device 80, an actuator button 122 protrudes through the housing 82 for easy access by the user. Other actuating means may also be used, some of which are described in more detail below.

Access to the vacuum pump 84, power source 86 and/or other components located within the evacuation device 80 may be accomplished through one or more access holes or panels (not shown) located in a side(s) of the evacuation device housing 82. Alternatively, the connecting face 82b of the evacuation device housing 82 may comprise a removable plate 124 that can be detached as needed to provide access to the vacuum pump 84, power source 86, and/or other components located within the evacuation device housing 82 (e.g., a microprocessor, radio, vacuum sensor, pushbutton switch, check valve, or filter). Since the evacuation device 80 is a structural part of the prosthesis, contains electronic components and, optionally, may contain a radio, it is preferable that in addition to having sufficient strength, the vacuum device be water resistant (more preferably, waterproof) and not interfere with radio transmissions.

It should be noted that another novel and beneficial feature of this embodiment of the present invention is the use of the universal distal adapter 88. As mentioned briefly above, such a distal adapter can allow for the interchangeability of various suspension devices, such as the evacuation device, a pin lock device, or a locking lanyard device. Each such device employs the same hole pattern so as to properly mate with the distal adapter 88. The aperture 90 in the distal adapter is of sufficient size to allow the passage of a suspension component (e.g., a locking pin or lanyard), but can also be sealed (as described above) when suction suspension is employed.

Figure 21:
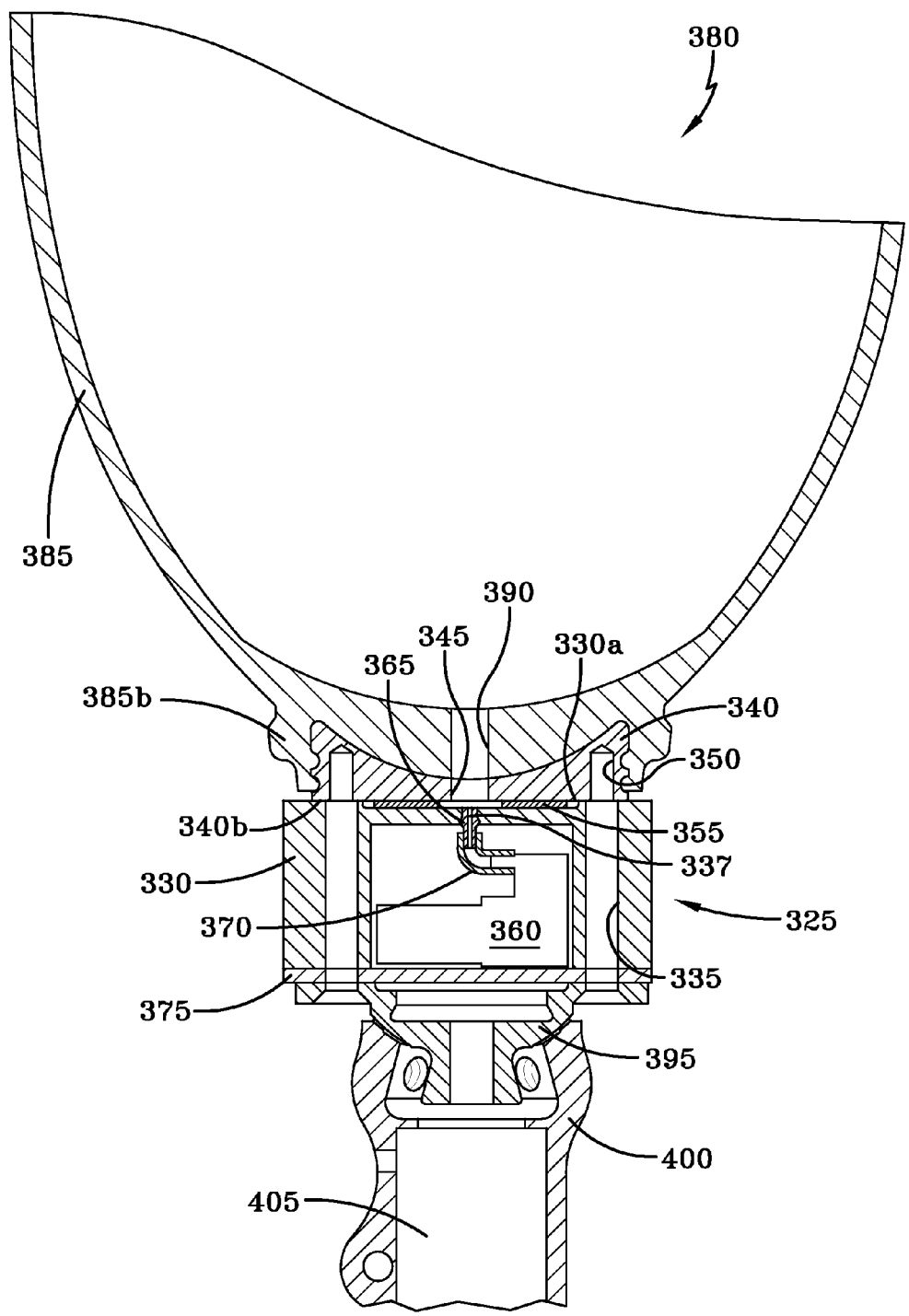
FIG. 21 is a cross-sectional view showing a portion of a prosthetic limb employing an alternate embodiment of an evacuation device that is similar to the evacuation device of FIGS. 7-12, and again includes a vacuum pump and power source that are located within a housing designed for attachment to a universal distal adapter that is built into the distal end of a prosthetic socket.

An alternate version of an evacuation device 325 of the present invention is shown in cross-section in FIG. 21. This evacuation device 325 is similar to the evacuation device 80 of FIGS. 7-12. However, as can be seen, the upwardly projecting sealing extension 102 of the previously described evacuation device 80 is absent from the mounting face of this evacuation device 325. Likewise there is also no aperture in the corresponding universal distal adapter 340 for receiving such an upwardly projecting sealing extension.

This evacuation device 325 can be seen to again have an evacuation device housing 330 adapted for mounting between the exterior distal end of a prosthetic socket 385 and a pylon 405 or other connecting component forming a portion of the remainder of the prosthetic limb 380. In this particular embodiment, the evacuation device 325 is associated with a prosthetic leg and is located between the distal end of the prosthetic socket 385 and a pyramid adapter 395. One end of the pyramid adapter 395 is secured to a bottom surface 330*b* of the evacuation device housing 330 by fasteners that are used to secure the evacuation device 325 to the socket 385 (see below). The other end of the pyramid adapter 395 is received by a pyramid receiver tube clamp 400 that connects a pylon 405 and the remainder of the prosthetic leg to the pyramid adapter and to the prosthetic socket.

This distal adapter 340 is similar to the distal adapter 88 described above and is again installed into the distal end 385*b* of the prosthetic socket 385. Preferably, a bottom surface 340*b* of the distal adapter 340 extends slightly from the exterior surface of the distal end 385*b* of the prosthetic socket 385. Alternatively, the bottom surface 340*b* of the distal adapter 340 may also be flush with or slightly interior of the exterior surface of the distal end 385*b* of the prosthetic socket 385. The distal adapter 340 includes a thru-hole 345 that aligns with a thru-hole 390 passing through the distal end 385*b* of the socket 385. The thru-hole 390 in the socket 385 may be created during socket molding or afterward. Although the thru-holes 345, 390 are shown to be substantially axially located in this embodiment, they could obviously be offset therefrom instead.

The evacuation device housing 330 again includes a number of mounting holes 335 that align with the corresponding mounting holes 350 in the distal adapter 340, and allow the evacuation device 325 to be secured thereto. Preferably, the mounting holes 335 in the evacuation device housing 330 are thru-holes and the mounting holes 345 in the distal adapter 340 are threaded to receive like-threaded fasteners (not shown). In order to seal the top surface 330*a* of the evacuation device housing 330 to the exterior of the distal end 385 of the prosthetic socket 385, a gasket 355 is preferably located therebetween.

A vacuum pump 360 is once again located within the evacuation device housing 330. The evacuation device housing 330 includes a vacuum passage (aperture) 337 that allows for communication between the vacuum pump 360 and the vacuum passageway formed by the aligned thru-holes 345, 390 in the universal adapter 340 and prosthetic socket 385.

The vacuum pump 360 is connected to the vacuum passage (thru-hole) 345 in the universal adapter 340. In this particular embodiment, the connection is made by inserting a barbed fitting 365 into the thru-hole 345 in the distal adapter 340 and connecting the vacuum pump 360 thereto with a piece of flexible tubing 370. Various other means of connecting the vacuum pump 360 to the thru-hole 345 in the distal adapter 345 may also be employed. For example, other types of fittings may be used, tubing may be inserted directly into the distal adapter thru-hole 345, or the vacuum pump 360 may be adapted for direct connection to the distal adapter thru-hole. In any event, the vacuum pump 360 is operative to evacuate the interior of the prosthetic socket 385 by drawing air therefrom via the thru-holes 390, 345 in the distal end 385*b* of the prosthetic socket and in the distal adapter 340.

Any or all of the other features described above with respect to the evacuation device 80 of FIGS. 7-12 may be possessed by this embodiment of the evacuation device 325. For example, and without limitation, a power source may be present within the evacuation device housing 330, and a lid or similar cover 375 may be provided thereon/therein to allow for access to the interior of the housing. Furthermore, this evacuation device housing 325 may employ the 4-hole mounting pattern of the evacuation device 80 of FIGS. 7-12, and may again be constructed of a material having sufficient strength and/or a material that does not interfere with radio signals. Evacuated air may be exhausted by the vacuum pump 360 in any manner previously described, or in another manner that would be known by one skilled in the art.

Figure 13:
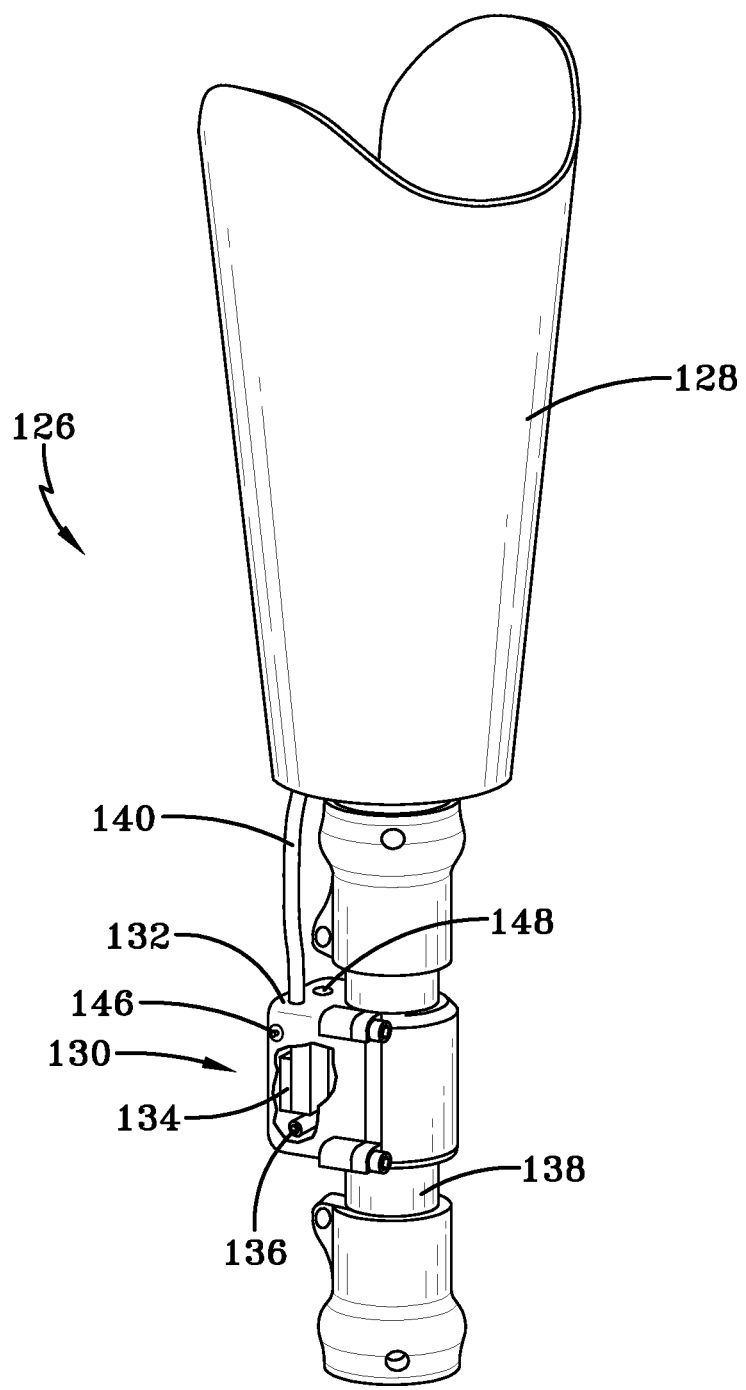
FIG. 13 depicts another embodiment of the present invention, wherein an evacuation device includes a vacuum pump and power source located within a housing that is mounted around the pylon of a prosthetic limb.

Another embodiment of the present invention is illustrated in FIG. 13. In this embodiment, a prosthetic limb 126 includes an evacuation device 130 for evacuating a prosthetic socket 128. The evacuation device 130 includes a housing 132 containing at least a vacuum pump 134 and power source 136. The housing 132 is designed to fit around a prosthetic pylon 138. As shown, the housing 132 may have two halves that can be fastened together around the pylon 138. In a variation of such an evacuation device, a housing may be of substantially one-piece construction having a passageway therethrough for receiving a pylon. Such a housing may be retained on the pylon through an interference fit, or by a clamping means, for example.

Although shown to be substantially rectangular in cross-section in FIG. 13, the housing 132 may be contoured. For example, the housing 132 may be contoured in a similar fashion to a human calf, or some other appropriate or pleasing shape.

In this embodiment of the present invention, the vacuum pump 134 may be connected to the interior of the socket 128 by a vacuum line 140 that runs through the pylon 138—in which case an aperture is provided through the pylon for passage of the vacuum line. Alternatively, and as shown, the vacuum line 140 may extend from the vacuum pump 134, through the housing 132 and distal end of the socket 128, and into the socket interior. As yet another alternative, a vacuum line 140 may extend from the vacuum pump 134, through the housing 132, and to a manifold (such as the manifold 290 described in detail below), which manifold provides for communication with the socket interior so that air can be drawn therefrom.

An actuator button 146 may extend through the housing for easy access by the user. Other actuating means may also be, some of which are described in more detail below.

Air evacuated from the socket may be discharged by the vacuum pump 134 through an exhaust port 148. The exhaust port 148 may reside at various locations in the housing 132. A one-way valve and/or muffler can be associated with the exhaust port 148.

Access to the vacuum pump 134, power source 136 and/or other components located within the evacuation device housing 132 may be accomplished by separating the halves of the evacuation device housing.

Figure 14A:
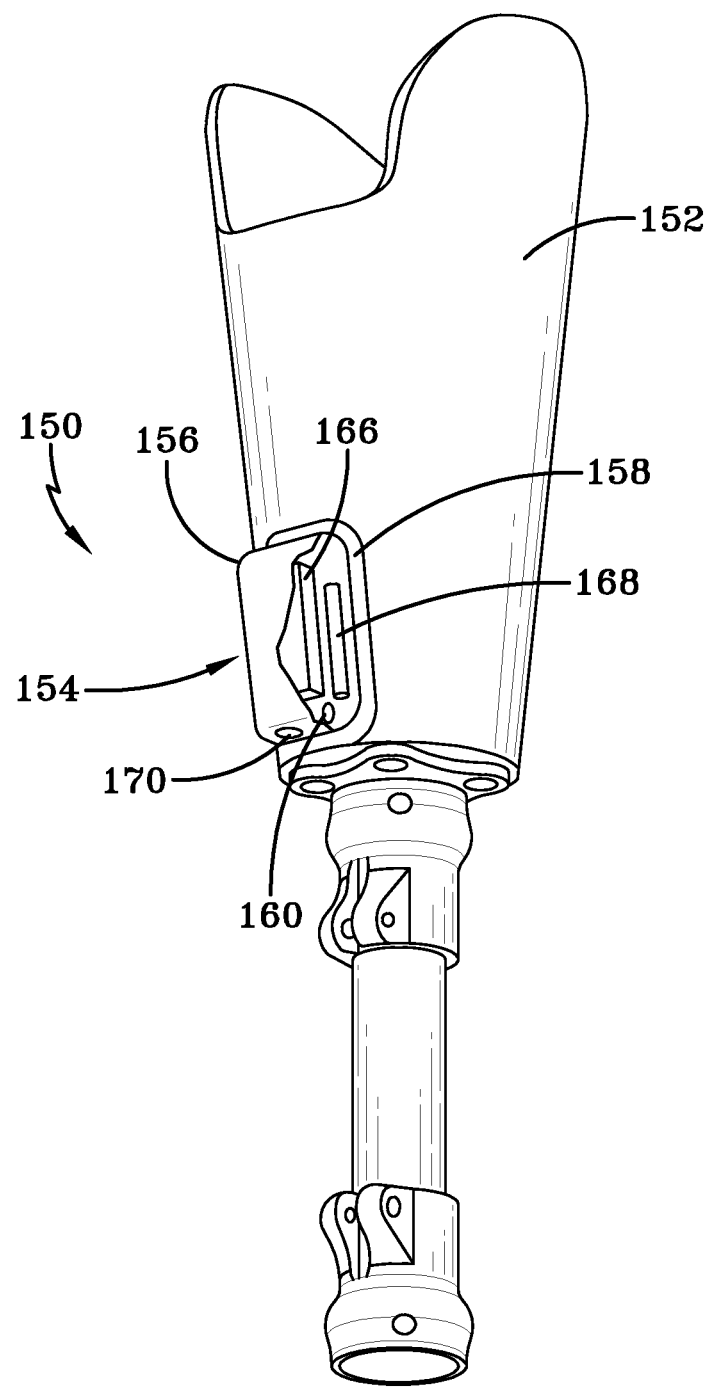
FIG. 14A shows another embodiment of the present invention, wherein an evacuation device includes a vacuum pump and power source located in a housing that is attached to an adapter integrated into a side wall of a prosthetic socket.

Another embodiment of the present invention is shown in FIG. 14A. In this embodiment, an evacuation device 154 includes at least a vacuum pump 166 and power source 168 contained within a housing 156 that is attached to a side wall of a socket 152 of a prosthetic limb 150. Preferably, the housing 156 is affixed to a mounting adapter 158 that is built directly into the socket 152, such as during the lamination thereof.

A vacuum passage 160 may extend through the mounting adapter 158 and socket sidewall, and into to the interior of the socket 152. Air may be evacuated from the socket interior by drawing it through the vacuum passage 160 using the vacuum pump 166.

Air evacuated from the socket 152 may be discharged by the vacuum pump 166 through an exhaust port 170. The exhaust port 170 may reside at various locations in the housing 156 or in the mounting adapter 158. When a manifold is used, an exhaust port may be located therein. A one-way valve and/or muffler can be associated with the exhaust port 170 regardless of its location.

Figure 14B:
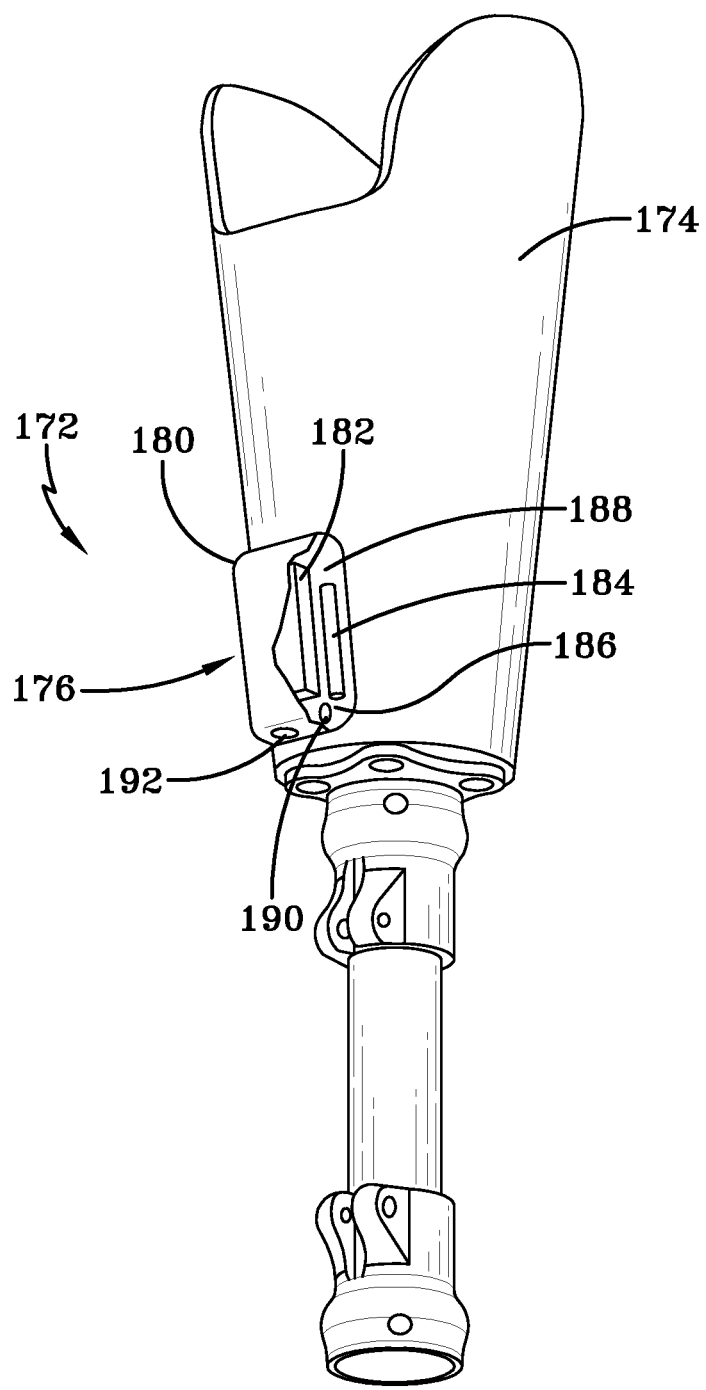
FIG. 14B shows another embodiment of the present invention, wherein an evacuation device includes a vacuum pump and power source located in a chamber that is integral to and protrudes from the side wall of a prosthetic socket.

A similar but additional embodiment of the present invention can be observed in FIG. 14B. In this embodiment, a prosthetic limb 172 is provided with an evacuation device 176 comprised of at least a vacuum pump 182 and power source 184 residing within a housing 180 that is integral to a side wall of a prosthetic socket 174. The housing 180 protrudes from the side wall of the socket 174 and forms a chamber 186 within which the vacuum pump 182 and power source 184 are retained. The housing 180 may be a separate component that is laminated or otherwise bonded to the socket 174 after the socket is formed. Preferably, however, the housing 180 is formed along with the socket 174.

The vacuum pump 182 and power source 184 may be permanently sealed within the chamber 186. Alternatively, a removable interior cover 188 may be provided to ensure that the vacuum pump 182, power source 184, and any other associated components remain within the chamber 186, while allowing access thereto when required.

A vacuum passage 190 or vacuum line may extend into the interior of the socket 174. When an interior cover 188 is present, the vacuum passage 190 or a vacuum line may extend therethrough. Air is evacuated from the socket interior by the vacuum pump 182 via the vacuum passage 190.

Air evacuated from the socket may be discharged by the vacuum pump 182 through an exhaust port 192. The exhaust port 192 may reside at various locations in the housing 180. A one-way valve and/or muffler can be associated with the exhaust port 192.

Figure 19:
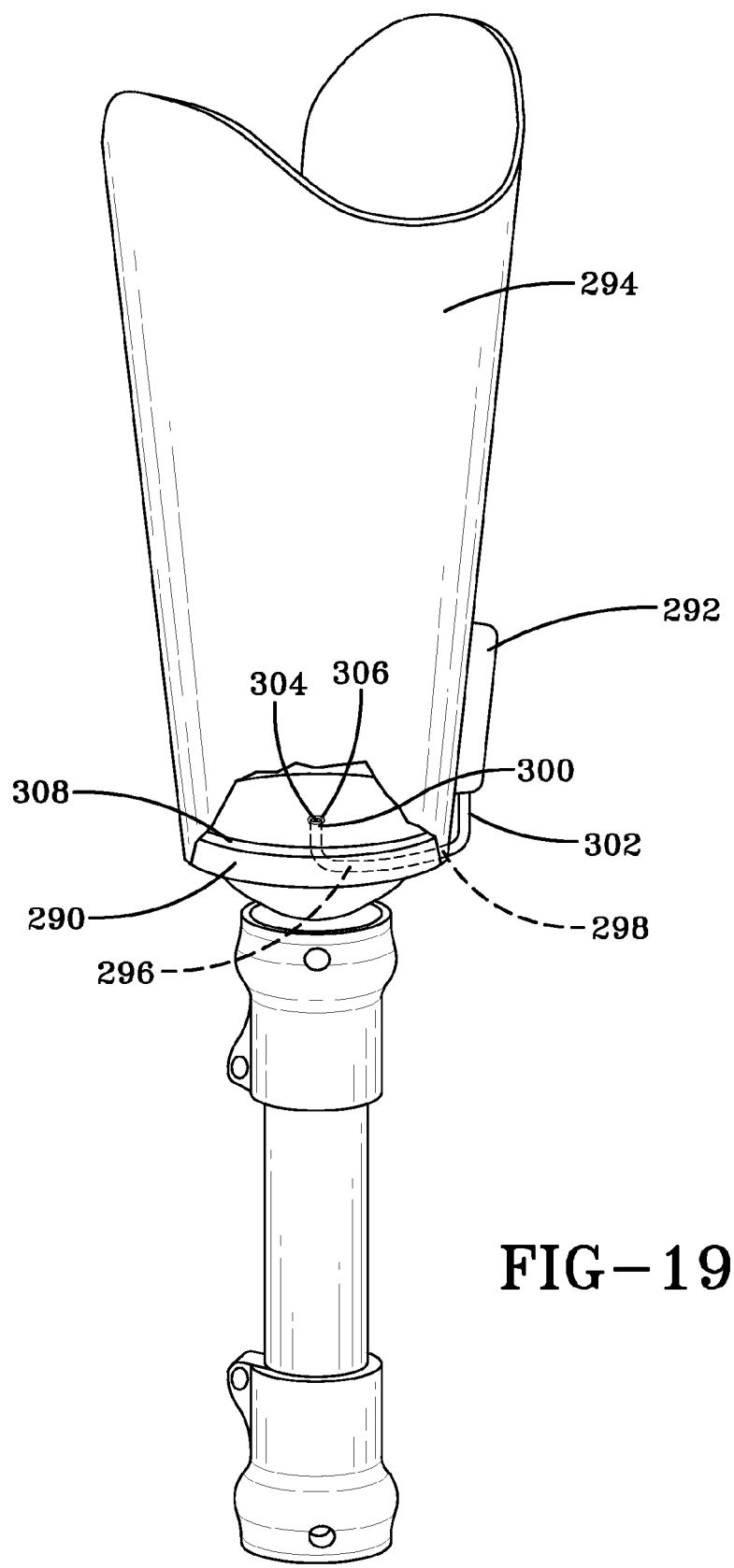
FIG. 19 depicts yet another embodiment of the present invention, wherein a manifold connects a vacuum source to the interior of a prosthetic socket.

In a variation of the embodiments shown and described with respect to FIGS. 14A and 14B, a vacuum line may run from the vacuum pump 166, 182, through the housing 156, 180, and to a manifold connected to the socket 152, 174, such as, for example, the manifold 290 depicted in FIG. 19. The manifold provides access to the interior of the socket 152, 174, such that air may be drawn therefrom by the vacuum pump 166, 182. In yet another variation, a vacuum line may run from the vacuum pump 166, 182, through the housing 156, 180, and to a vacuum passage located more remotely from the evacuation device, such as on the bottom surface of the socket.

Figure 15:
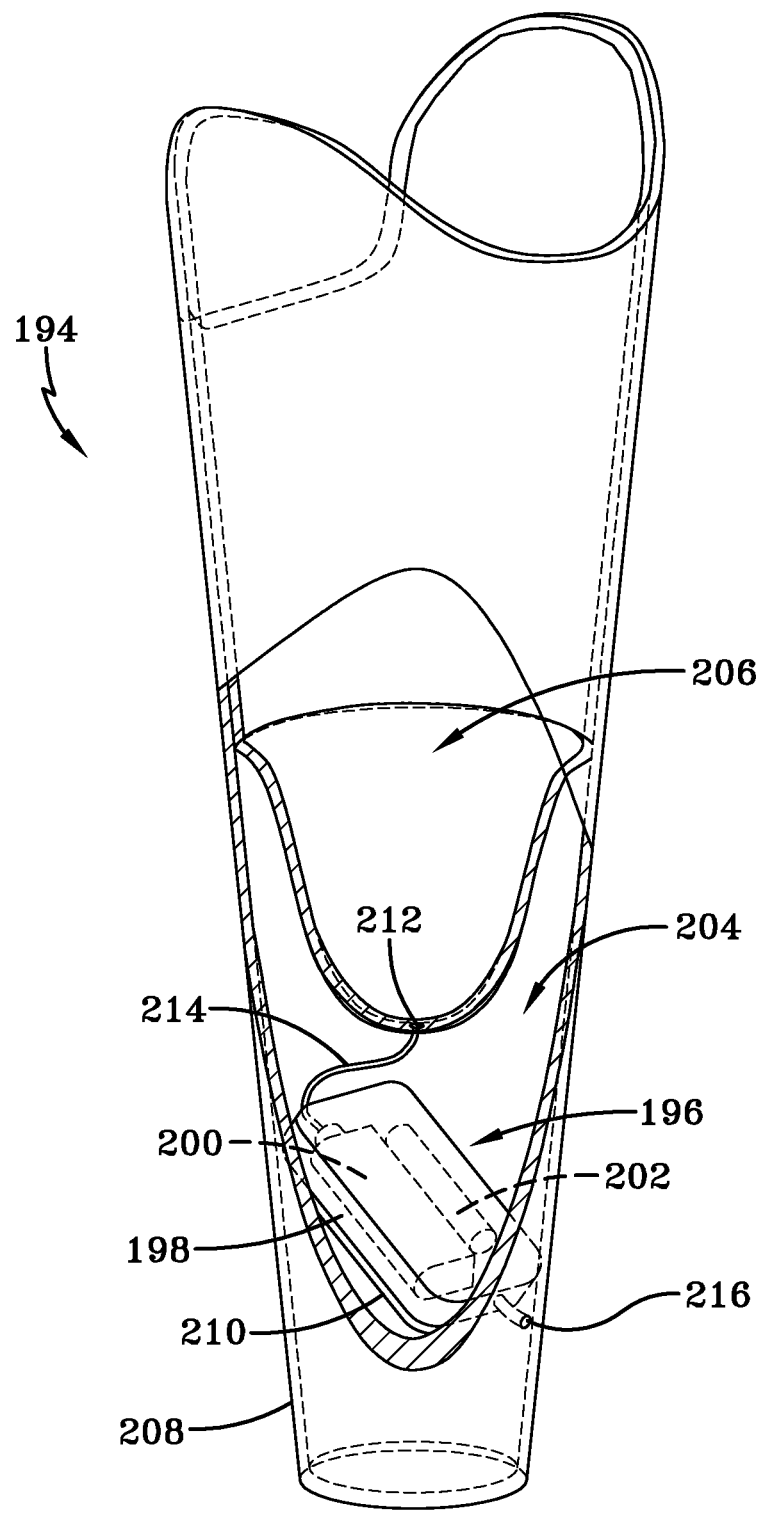
FIG. 15 illustrates another embodiment of the present invention, wherein an evacuation device includes a vacuum pump and power source located in a housing that is positioned within an exoskeletal prosthetic device.

Another alternative embodiment of the present invention can be seen in FIG. 15. In this embodiment, an evacuation device 196 including at least a vacuum pump 200 and power source 202 located in a housing 198, is positioned within an exoskeletal prosthetic device 194. More specifically, the housing 198 is located within a cavity 204 between a socket portion 206 and distal end 208 of the exoskeletal prosthetic device 194. Such an exoskeletal prosthetic device 194 may account for a majority of a prosthetic leg or prosthetic arm, for example.

The evacuation device 196 may be secured within the exoskeletal prosthetic device 194 in any number of ways. For example, when the evacuation device 196 includes a housing 198, straps, clips, tabs, releasable adhesives, Velcro®, and any number of other types of retainers may be secured to the interior of the exoskeletal prosthetic device 194 and used to engage and retain the housing. Such retainers can also be provided to individually secure the vacuum pump 200 and power source 202 within the exoskeletal prosthetic device 194 in embodiments of the present invention wherein no evacuation device housing is used.

In a variation of this embodiment, a mounting pad, plate or other such structure may be fabricated or otherwise secured within the cavity 204 of the exoskeletal prosthetic device 194 to provide an attaching surface 210 for the housing. The housing 198 may be secured to the attaching surface 210 using any of the retainers mentioned above, or by screws, double-sided tape, or any other known means.

A vacuum passage 212 extends into the interior of the socket 206. A vacuum line 214 connects the vacuum pump 200 of the evacuation device 196 to the socket interior via the vacuum passage 212. Air is evacuated from the socket interior by the vacuum pump 200 using the vacuum passage 212 and vacuum line 214.

Air drawn from the socket interior may be discharged by the vacuum pump 200 directly to the atmosphere through an exhaust port 216 in the exoskeletal prosthetic device 194. Alternatively, air evacuated from the socket interior may be discharged into the cavity 204 in the exoskeletal prosthetic device 194, where it may thereafter leak to the atmosphere through one or more component interfaces or be released through the exhaust port 216 which, in this case, may be manually or automatically actuatable. Any exhaust port associated with any variation of this embodiment of the present invention may include a one-way valve and/or muffler.

Figure 16:
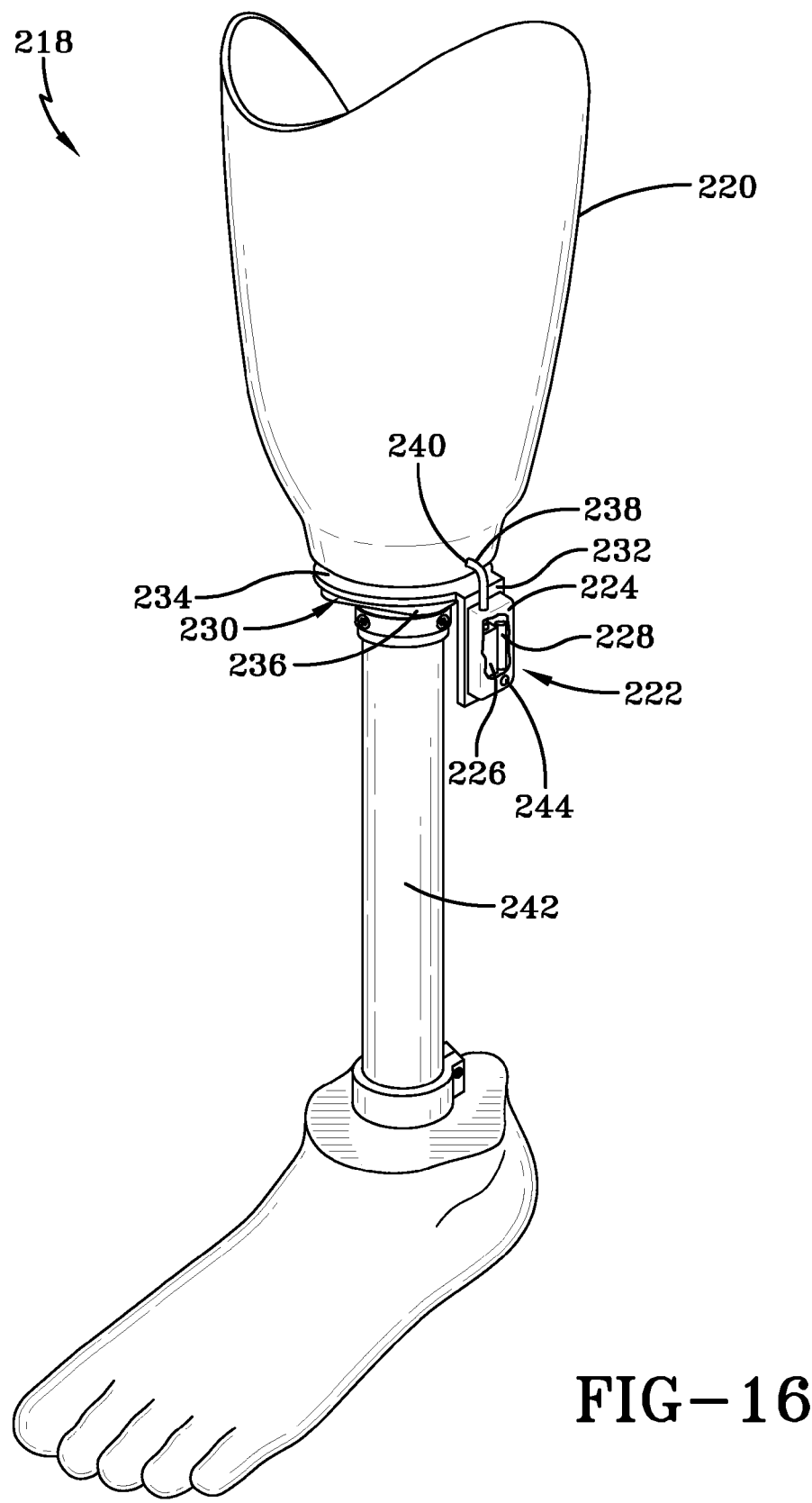
FIG. 16 depicts another embodiment of the present invention, wherein an evacuation device includes a vacuum pump and power source located in a housing that is affixed to a mounting plate designed to be mounted between adjacent components of a prosthetic limb.

FIG. 16 depicts another embodiment of the present invention, wherein an evacuation device 222 is affixed to a mounting plate 230 that is designed to be mounted between adjacent components of a prosthetic limb 218. Preferably, the evacuation device 222 includes a housing 224 that contains at least a vacuum pump 226 and power source 228, the housing adapted for affixation to an attachment face 232 of the mounting plate 230. Alternatively, the vacuum pump 226 and power source 228 may be individually affixed to the attachment face 232 of the mounting plate 230 without a housing.

The mounting plate 230 is preferably L-shaped, such that a mounting portion 234 thereof can be located between adjacent components of the prosthetic limb 218, while the attachment face 232 extends substantially parallel to the length of the prosthetic limb. The mounting plate 230 may be located between for example, without limitation, a prosthetic ankle and foot, or a prosthetic socket 220 and a pyramid adapter 236.

A vacuum line 238 may run from the vacuum pump 226, through the housing 224, if present, and into a vacuum passage 240 located in the socket 220 of the prosthetic limb 218. The vacuum line 238 may run between the vacuum pump 226 and socket 220 completely exterior to the prosthetic limb 218, as shown, or may be routed at least partially within the mounting portion 234, a pylon 242, and/or other components of the prosthetic limb. Those portions of the vacuum line 238 that run exterior to the prosthetic limb 218 are preferably, but not necessarily, releasably secured to neighboring limb components.

In a variation of this embodiment, a vacuum line may run from the vacuum pump 226 (through the housing 224, if present) to a manifold connected to the socket 220, such as, for example, the manifold 290 depicted in FIG. 19. The manifold provides access to the interior of the socket 220, such that air can be drawn therefrom. When a manifold is used, any of the above-described routings of the vacuum line 238 may be employed.

Air evacuated from the socket 220 may be discharged to the atmosphere by the vacuum pump 226. The evacuated air may be discharged through an exhaust port 244, which may be located in/on the vacuum pump 226, or at various locations in the housing 224 (if present). When a manifold is used, an exhaust port may be located therein. A one-way valve and/or muffler can be associated with the exhaust port, regardless of its location.

Figure 17:
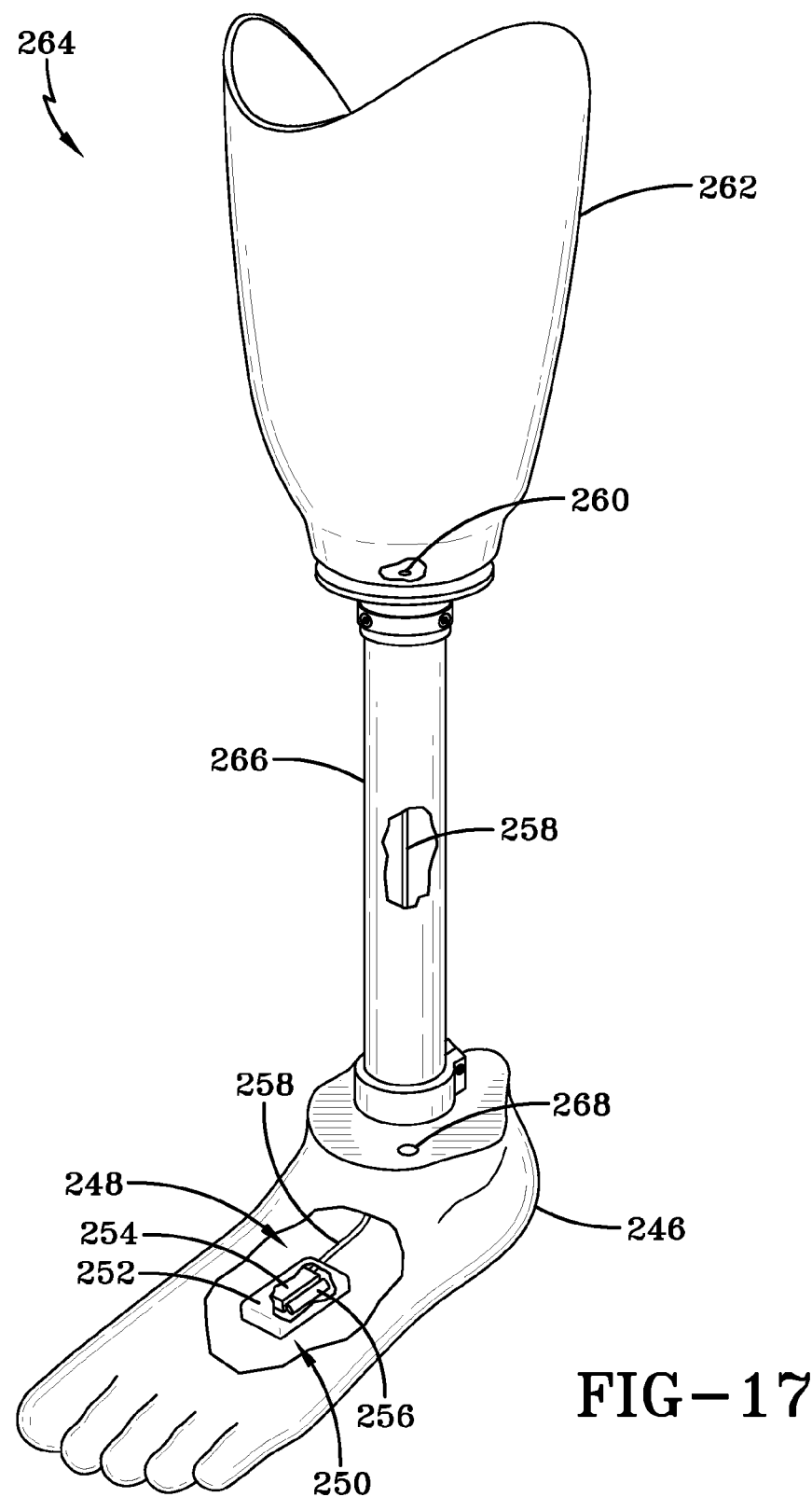
FIG. 17 shows another embodiment of the present invention wherein an evacuation device includes a vacuum pump and power source located in a prosthetic foot or within a housing that is positioned in a prosthetic foot.

FIG. 17 shows another embodiment of the present invention wherein an evacuation device 250 is located within a prosthetic foot 246 (which may be a solid prosthetic foot or a hollow foot covering). For example, the evacuation device 250 may consist of a vacuum pump 254 and associated power source 256 that reside within a cavity 248 in the foot 246. Preferably, however, the evacuation device 250 also includes a housing 252 that contains the vacuum pump 254 and power source 256 and is located in the prosthetic foot cavity 248.

A vacuum line 258 may run from the vacuum pump 254, through the prosthetic foot 246, and into a vacuum passage 260 located in the socket 262 of the prosthetic limb 264. The vacuum line 258 may run between the vacuum pump 254 and socket 262 completely exterior to the prosthetic limb 264, as shown, or may be routed at least partially within a pylon 266 and/or other components of the prosthetic limb. As an example of this latter construction, the vacuum line 258 might be routed from within the foot through a prosthetic ankle and pylon, and into the distal end of the socket. Those portions of the vacuum line 258 that run exterior to the prosthetic limb 264 are preferably, but not necessarily, releasably secured to neighboring limb components.

In a variation of this embodiment, the vacuum line 258 may run from the vacuum pump 254 to a manifold connected to the socket 262, such as, for example, the manifold 290 depicted in FIG. 19. The manifold provides access to the interior of the socket 262, such that air can be drawn therefrom. When a manifold is used, either of the above-described routings of the vacuum line 258 may be employed.

Air evacuated from the socket by the vacuum pump 254 may be discharged to the atmosphere, preferably through an exhaust port 268 located in the prosthetic foot 246. When a manifold is used, an exhaust port may be located therein. A one-way valve and/or muffler can be associated with the exhaust port, regardless of its location.

Figure 18:
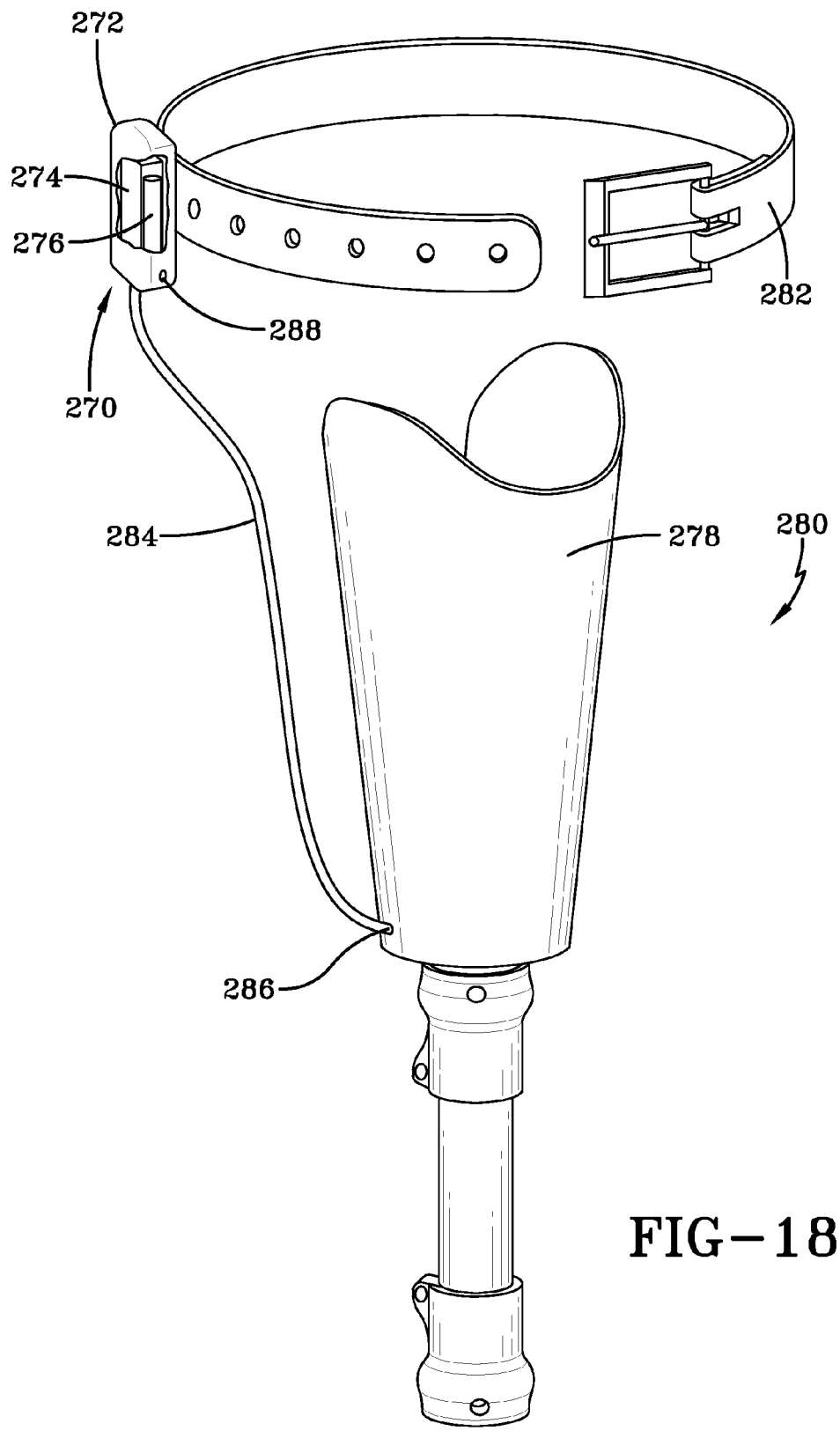
FIG. 18 illustrates another embodiment of the present invention, wherein an evacuation device includes a vacuum pump and power source located within a housing that is located on the user's person and provided to evacuate the socket of a prosthetic limb.

FIG. 18 illustrates another alternative embodiment of the present invention, wherein an evacuation device 270 includes a housing 272 containing at least a vacuum pump 274 and power source 276, the evacuation device being located on the user's person and provided to evacuate a socket 278 of a prosthetic limb 280.

As shown in FIG. 18, this embodiment of the evacuation device 270 may clipped or otherwise attached to a user's belt 282. Alternatively, the evacuation device 270 may be placed in a pocket or temporarily attached to some other piece of a user's attire. The housing 272 may have an attachment mechanism such as a spring-loaded clip integral thereto or, alternatively, the housing may fit into a sleeve or similar holder that acts to temporarily secure the evacuation device 270 to a user's attire. Such a holder may operate, for example, much like a clip-on cell phone holder.

A vacuum line 284 may run from the vacuum pump 274, through the housing 272, and into a vacuum passage 286 located in the socket 278 of the prosthetic limb 280. The vacuum line 284 may be routed at least partially under the user's clothing. Those portions of the vacuum line 284 that run exterior to the prosthetic limb 280 are preferably, but not necessarily, releasably secured to the prosthetic socket 278.

In a variation of this embodiment, the vacuum line 284 may run from the vacuum pump 274 to a manifold connected to the socket 278, such as, for example, the manifold 290 depicted in FIG. 19. The manifold provides access to the interior of the socket 278, such that air can be drawn therefrom.

Air evacuated from the socket 278 by the vacuum pump 274 may be discharged to the atmosphere, preferably through an exhaust port 288 located in the housing 272. When a manifold is used, an exhaust port may be located therein. A one-way valve and/or muffler can be associated with the exhaust port, regardless of its location.

FIG. 19 depicts yet another embodiment of the present invention, wherein a manifold 290 is provided to connect a vacuum source 292 to the interior of a prosthetic socket 294. The vacuum source 292 may be an evacuation device of the present invention, a hand-operated vacuum pump, or some other vacuum device that can be connected to the manifold 290.

In the particular embodiment shown in FIG. 19, the manifold 290 is associated with and attached to the distal end of the prosthetic socket 294. It should be realized, however, that it would also be possible to attach such a manifold to other portions of the prosthetic socket 294, as long as the attached location permits access to the interior portion of the socket that is to be evacuated.

As can be observed, a vacuum passageway 296 extends through the manifold 290. One end 298 of the vacuum passageway 296 is adapted to connect with or receive a vacuum line 302 that connects the manifold 290 to the vacuum source 292. The other end 300 of the vacuum passageway 296 is adapted to align with a vacuum passage 304 that extends through the socket wall. In this embodiment, the vacuum passage 304 extends through the distal end of the socket 294, but could be located elsewhere in other embodiments. An o-ring 306 or other sealing element may be located at the interface of the vacuum passageway 296 and the vacuum passage 304 to help ensure an air-tight seal.

The manifold 290 may be attached to the socket 294 in a number of different ways. For example, the manifold 290 may be laminated or otherwise bonded to the socket 294. Alternatively, the manifold 290 may be secured to a mounting plate 308 that has been integrated into the socket 294. The manifold 290 could also be affixed to the universal distal adapter 88 shown in FIGS. 8-12.

Using the vacuum source 292, air is drawn from the socket interior through the manifold 290. The evacuated air may be discharged through an exhaust port associated with the vacuum source 292 or from some other location. As described above, a one-way valve and/or muffler can be associated with the exhaust port, regardless of its location.

Figure 20:
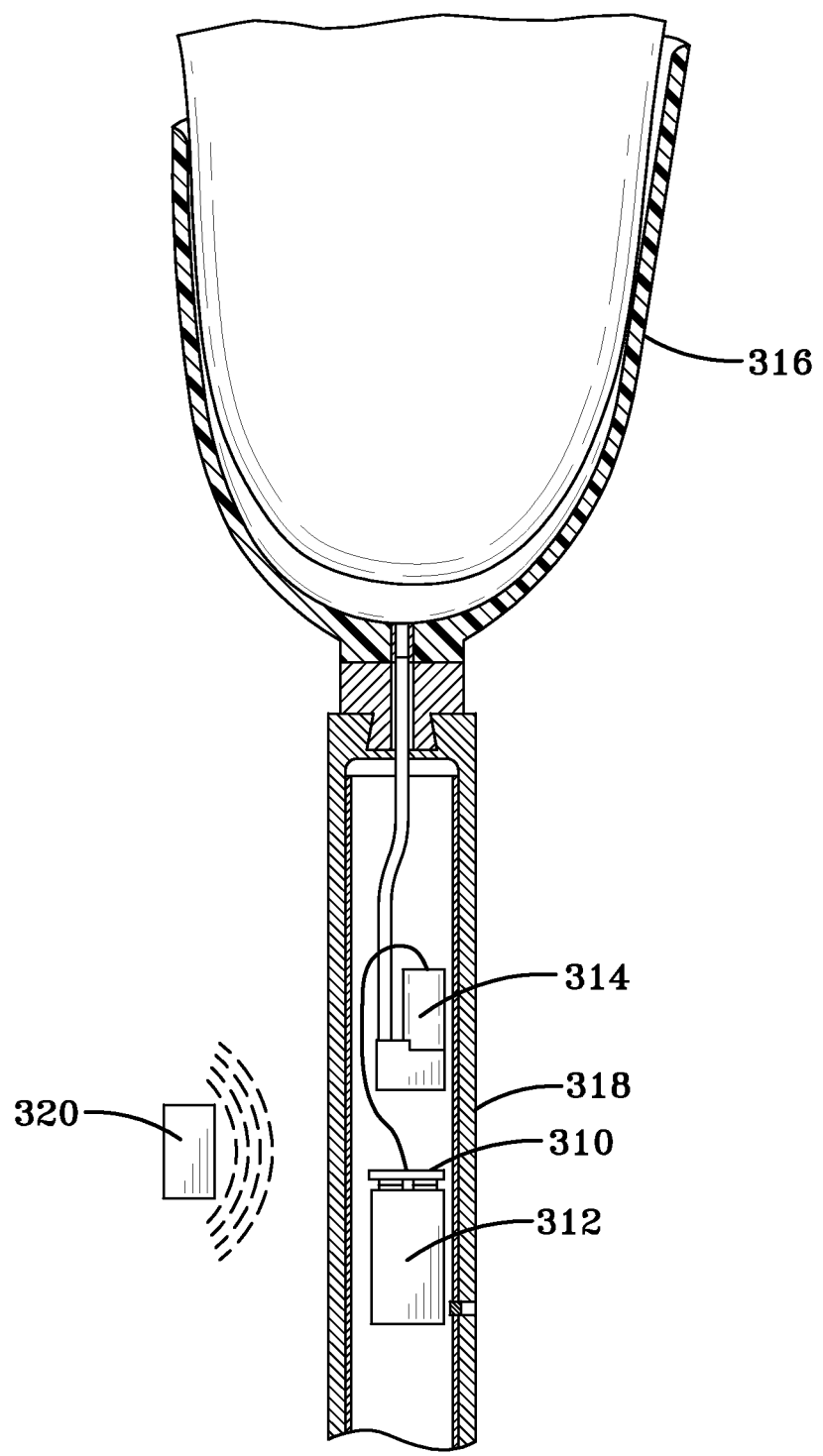
FIG. 20 shows a magnetic switch that can be used to initiate the energizing of a vacuum pump in any embodiment of the present invention.

As generally illustrated in FIG. 20, a magnetic switch 310 may be used in place of an actuator button or other vacuum pump actuator that requires direct contact by the user. As shown, the magnetic switch 310 resides between a power source 312 and a motor of a vacuum pump 314. When actuated, the magnetic switch 310 allows current to flow from the power source 312 to the motor, activating the vacuum pump 314 and initiating the evacuation process.

Unlike a protruding pushbutton or switch, however, actuation of the magnetic switch 310 can often take place through the material forming, for example, an evacuation device housing (see above), a prosthetic socket 316, or a prosthetic pylon 318 (as shown). More specifically, in many embodiments of the present invention, a user can activate and deactivate the evacuation device simply by holding a small magnetic activator 320 in close proximity to the magnetic switch 310. Magnetic attraction between the magnetic activator 320 and the magnetic switch 310 either activates or deactivates the evacuation device as desired. Selective activation and deactivation can be accomplished, for example, by reversing the field of the magnetic activator 320 or by changing the location thereof with respect to the magnetic switch 310.

As mentioned previously, a vacuum pump of the present invention may be operated by various power sources, such as one or more batteries or capacitors. As one of the main detractions to the use of electronic devices in prosthetics is the need to eventually replace the power source, however, evacuation devices of the present invention are preferably provided with easy access to the power source(s) and/or, more preferably, employ a rechargeable power source(s).

When employing a rechargeable power source, recharging can be accomplished by either direct or inductive charging. In the most simplistic form of direct charging, the power source is connected to a plug-in charger that transfers electrical energy to the power source using the electrical circuitry of the evacuation device. For example, an evacuation device may have a housing that includes a charging jack that is connected to the contacts of the power source. The power source of such an embodiment can then be recharged simply by plugging an external charger into the charging jack.

Ideally, it is desirable for the user of an evacuation device of the present invention to never have to worry about charging of the power source. That is, even when a simplistic means for direct charging is provided, a user would still have to monitor or otherwise be informed of the charge status of the power source, and act accordingly if the charge level reaches a sufficiently low level.

To eliminate this requirement, it is possible to provide an evacuation device of the present invention with self-charging capabilities. For example, a small inductive generator may be located on the prosthetic limb and placed in electrical communication with the evacuation device power source. Such a generator may be constructed and located on the prosthetic limb such that movement of the prosthetic limb during ambulation of the amputee will generate electric power by causing relative motion of coils within a magnetic field. Electrical energy produced by the generator is then provided to the evacuation device power source to maintain the power source in an acceptably charged state.

Other types of electric power generators may be employed for the same purpose. For example, an electro active polymer (EAP) generator could be associated with the prosthetic limb. EAP materials have evolved into a very viable alternative to other energy generation methods, and although EAP generators do have some limitations, these limitations are not insurmountable in a prosthetic device application. Alternatively, sufficient charging energy could also be generated using piezoelectric element generators. Piezoelectric elements generate a voltage in response to applied mechanical stress and, therefore, can be caused to generate electrical energy by movement of a prosthetic limb to which they are attached.

Consequently, any evacuation device embodiment of the present invention can be provided with such self-charging capability. When so equipped, an evacuation device of the present invention also includes any electrical circuitry necessary to receive electrical energy from the generator(s), and may also include circuitry and/or other elements to prevent over-charging of the power source(s).

With respect to the operational aspects of the evacuation devices of the present invention, each embodiment may include basic through advanced versions thereof. More particularly, each embodiment of an evacuation device of the present invention may include a basic version that provides for manual operation only, an advanced version that is fully automatic, and one or more versions having operational features that fall somewhere therebetween.

At the basic level, each embodiment of an evacuation device of the present invention can provide for manual operation. Manual operation essentially involves a user engaging an actuator that results in activation of a vacuum pump and evacuation of the prosthetic socket. The vacuum pump will continue to evacuate the socket until the user releases the actuator or the vacuum level reaches the maximum level that can be achieved by the pump. Thus, manual operation allows a user to select a vacuum level that best corresponds to his/her current activity level or desired comfort level. Vacuum can be periodically increased or decreased as desired by the user.

Each embodiment of an evacuation device of the present invention may also operate in a semi-automatic mode. This can be achieved by adding certain types of sensors to the vacuum system, thereby requiring only minimal user interaction. For example, in a simplistic embodiment of semi-automatic operation, a pressure switch may be provided and simply configured to prevent the vacuum level from exceeding some level previously found to be uncomfortable or otherwise inappropriate for the user.

However, a more effective method of controlling the system involves using a pressure sensor to monitor vacuum level. While an absolute vacuum pressure sensor could be used for this purpose, there are drawbacks associated therewith. Primarily, the use of an absolute pressure sensor would result in an amputee experiencing significantly different inter-socket forces as a result of elevation changes. Such force differences would be exacerbated by extreme changes in elevation, such as between sea level and a high ground level (e.g., such as in Denver Colo.), or between a ground level altitude and the altitude achieved during airplane flight. Therefore, the monitored pressure is ideally a gauge pressure—with a pressure gauge exposed to ambient air pressure, or a differential pressure sensor referenced against the ambient air pressure. In contrast to a system control design that uses an absolute pressure sensor, these latter sensor configurations will provide a direct link between the controlled vacuum pressure and the actual pressures and forces experienced by a user of the system. Due to its small size, differential capability, surface mount configuration, and temperature compensation, it has been determined that the model 26PC15SMT sensor manufactured by Honeywell is a particularly well suited for such use. Other acceptable sensors are also available.

In another particular embodiment of semi-automatic operation, a vacuum pump is preset to draw a particular level of vacuum once activated. Therefore, the single intermittent push of a push-button or other actuator will cause the vacuum pump to operate until an associated pressure sensor determines that the desired pressure has been met. It is also possible to mix modes of operation by allowing the user to enter a semi-automatic mode with a quick contact of the actuator, but to enter a manual mode by prolonged contact with the actuator.

Operation of an evacuation device of the present invention can be further enhanced by adding either logic, analog controls, or a microprocessor 502. With such an addition, it is possible to monitor socket pressure and automatically maintain the socket pressure within a patient or practitioner defined range of acceptable pressures. This automatic mode of operation completely eliminates the need for the user to monitor the socket pressure, and the prosthetic limb then becomes a device that can simply be donned and forgotten until removal thereof is desired. It can be appreciated that such a vacuum suspension system will be able to automatically react to conditions within the socket in a manner appropriate for the user, and in ways not possible for a mechanical pump design.

The addition of sensors and a microprocessor to an evacuation device of the present invention and/or to a prosthetic limb equipped with such an evacuation device, permits the monitoring of various conditions or parameters of the prosthetic limb and/or the user. For example, by appropriately locating a basic pressure transducer in the prosthetic socket, the measuring and tracking of various pressure values associated with the prosthetic socket becomes possible. Pressure values of interest may include maximum or minimum socket pressure, the average pressure in the socket over some period of time, and the Root Mean Square (RMS) pressure over a defined period of time.

With respect to these latter values, the period of time monitored might depend on the conditions that the user or a practitioner is evaluating. For initial setup and function testing, for example, the time period might be set to a single step. For evaluation on more complicated tasks such as engaging in a sport or ascending/descending stairs, the time period might be extended to obtain a target range for all of the various ways that the activity at issue might be performed. The test period might even be extended to a period of days to track values for the user's entire range of activities. Another parameter that may be tracked is some measure of the amount of pressure the user is exposed to over the course of a period of time. Measure of this parameter would be the integral of pressure as a function of time, or the integral of the pressure squared as a function of time. With an appropriate link to the microprocessor, such data can then be displayed on a PC, a key fob device, or some other display unit for viewing and analysis by the user and/or practitioner. Of course, the data may also be saved for later reference.

Because a concern with any vacuum-based prosthetic suspension system is the quality of the seal, this is another condition that may be monitored. While it is difficult to directly monitor the seal, it is possible to monitor the duty cycle of an automatically-controlled vacuum pump motor as the vacuum pump acts to maintain the vacuum level within the prosthetic socket. Increases in the duty cycle indicate increases in air leaks and a degradation of the seal. To properly monitor this condition, a base line vacuum pump duty cycle can be obtained during setup of the associated prosthesis. Monitoring the duty cycle and comparing it to this baseline will then provide a measure of the seal and allow its quality to be monitored.

Another mode of monitoring the prosthetic socket is a high speed real time mode. In this mode, vacuum level variations within the socket can be monitored in real time, as they occur. Data is then recorded relative to a known time base and allows vacuum fluctuations to be ascribed to specific events during the user's activities. This mode also allows graphical displays to be constructed that can be used to visualize the relationship between a user's activities and the vacuum level within the socket.

In microprocessor-equipped embodiments of the present invention wherein vacuum level within the socket is or can be monitored, it is also possible to monitor the range or variation of the vacuum level and make some judgments as to the user's activity level based thereon. In this manner, it is possible to then automatically adjust the level of vacuum to the level of activity of the user. For example, the vacuum level may be increased over the typical level for a user who becomes very active. Similarly, vacuum level may be automatically decreased if a user is substantially sedentary or non-ambulatory for some period of time, and then may be automatically increased when the user becomes more active. This method of monitoring the level of user activity and automatically adjusting the vacuum to a correlating level results in a system that continually attempts to keep the vacuum level in the socket at an appropriate level.

As would be understood to one skilled in the art, different phases of an amputee's gait cycle subject the socket of a prosthetic leg to different stresses, strains, accelerations, and impacts (this is similarly true during use of a prosthetic arm). The result is that during different phases of the gait cycle, the pressure in the socket and the sensations that the amputee experiences differ. For example, a level of vibration that would be noticeable during the free swing phase of gait, where vibrations are at a minimum, may not be noticeable if it occurs at the point of heel strike where other masking sensations are present.

Also, drawing a vacuum during the free swing phase of the gait cycle is more difficult to achieve and requires more electrical energy than does drawing a vacuum during the stance phase of the gait cycle. This is due primarily to the fact that the socket is in tension during the swing phase, while during the stance phase the socket is being driven back onto the amputee's residual limb—thereby effectively forcing air from the socket. For at least these reasons, it is advantageous to monitor a lower limb amputee's gait cycle. Movement of the upper limb of an upper extremity amputee can be similarly monitored. Simple tracking can be achieved by observing the pressure fluctuations in the socket and reacting thereto. When more reliable gait or other movement synchronization is desired, more complex evaluations can be achieved through the addition of accelerometers, gyroscopes, force sensors, or some combination thereof.

The use of a pushbutton, magnetic switch, and other simplistic actuators has been described above with respect to manually operable evacuation device embodiments of the present invention. However, other forms of evacuation device interfaces may also be used, whether in conjunction with such actuators or in place thereof.

In one very simplistic information-only interface, basic power, pressure, and functional information can be communicated to the user through simple LED indicators. Such an interface may continually display information, or it may display information only when the patient requests it in order to conserve power. Such a display can be built into the evacuation device housing, if present.

In another information-only interface, basic information regarding evacuation device function, etc., can be communicated to the user by means of an audio transducer. One benefit of this design is that it does not require the user to view the evacuation device or some other display unit associated therewith.

Pushbuttons (and similar switch-type devices) may be used in a very basic operating and/or programming interface. Pushbuttons are simple, easy to understand, and draw no power when they are not active. Used with a properly designed low-power microprocessor, pushbuttons account for very little power consumption. There are a number of types of switches or switch-type devices that could actually be used. Standard contact switches are one choice. Membrane-type switches may be a reliable, attractive, and space efficient alternative. Also, proximity or capacitive detection switches have recently become available that are able to detect "touches" through a closed container and, as such, would eliminate the need for a passage from the outside of an evacuation device housing or prosthetic component to the inside. Another possibility is a Hall-type device that operates by using some sort of magnetic key. Such a device might be used to provide simple on/off control, perhaps as a backup to other more advanced interfaces.

More complex interfaces may be associated with more complex evacuation devices of the present invention, such as the semi-automatic and automatic versions described above. One such interface may be comprised of a series of pushbuttons associated with the evacuation device. These pushbuttons may be located, for example, on an evacuation device housing. The disadvantage to such an interface, however, is that it requires the patient to remove clothing, or possibly cosmetic fittings, to activate the vacuum pump, update a program, or make changes to the vacuum settings.

In order to impart a more lifelike appearance thereto, amputees often prefer to finish their prosthesis with a cosmetic covering, which may be made of foam or other materials. However, as mentioned above, the application of a cosmetic covering to a prosthesis can inhibit access to certain embodiments of an evacuation system of the present invention, such as may be required for recharging, reprogramming, etc. Attempting to access such evacuation systems may be difficult and could potentially result in damage to the cosmetic covering.

As such, at least certain evacuation systems of the present invention may be modified to avoid such potential problems. One modification involves routing a programming/recharging cable 500 from the vacuum system controller to an unobtrusive and easier to access location, such as an ankle or inner thigh portion of the prosthesis. The free end of the programming/recharging cable 500 is provided with an appropriate connector that allows it to be connected to a programming and/or recharging device.

Notwithstanding the functionality of the foregoing exemplary embodiments, a more convenient method of interfacing with an evacuation device of the present invention is through a wireless link. Thus, an evacuation device of the present invention may include a radio, cellular or some other form of wireless transmitter/receiver. A wireless link with the transmitter may then be established in any of several ways.

In one embodiment, a stand-alone communication device is used to communicate with the evacuation device. Such a stand-alone communication device may be embodied in a hand held unit, such as a fob, which may include, among other things, an integrated transmitter/receiver, input keys, and an alphanumeric and/or graphical display. This design would allow a user to keep the fob in their pocket and to communicate with the evacuation device easily and inconspicuously. This also allows the user to observe actual operating conditions and parameters associated with the evacuation device and/or prosthesis, and to optimize evacuation device operation to best suit their needs.

One particular exemplary embodiment of a wireless communication-based control system 410 for an evacuation device of the present invention is electronically represented by the schematic diagrams of FIGS. 22a-22b. The diagram of FIG. 22a represents a vacuum control assembly 415 of the control system 410 that is associated with a prosthesis, while the diagram of FIG. 22b represents a hand held controller 420 (e.g., fob) portion of the control system. The vacuum control assembly 415 and the hand held controller 420 are wirelessly linked.

Wireless communication occurs in this particular embodiment via a wireless (e.g., radio) transceiver portion that is integral to a microprocessor unit 425, 430 located in the vacuum control assembly 415 and hand held controller 420, respectively. A number of microprocessors with integrated transceivers are commercially available, and would be known to one skilled in the art. In an alternative embodiment, a functional control system for an evacuation device of the present invention could be built using transceivers that are separate from their associated microprocessors. However, the integrated design offers the advantages of lower cost, less weight, and reduced circuit complexity.

As shown, each of the vacuum control assembly 415 and hand held controller 420 also respectively includes a regulator 435, 440 with an enable pin 445, 450, a power source 455, 460, and a self-latching power supply system. Additionally, the vacuum control assembly 415 separately includes a pressure sensor 465 and vacuum pump 470, while the hand held controller 420 separately includes a display 475. In this particular embodiment the display 475 of the hand held controller 420 is shown to be of the LCD variety. The use of other display types is also possible, however, power consumption associated therewith is preferably minimized. One LCD type display that has been found to be acceptable for use in this design is the model DV40311 LCD display manufactured by Densitron Displays of Santa Fe Springs, Calif.

Minimized power consumption can also be facilitated by proper selection of the microprocessors 425, 430 and timing crystals 480, 485 that are respectively associated with each of the vacuum control assembly 415 and hand held controller 420. For example, a number of low lower power consuming timing crystals are available, such as the model FC-135 32.7680KA-A3 crystal manufactured by Epson Electronics America, Inc. in Wakefield, Mass.

The use of a regulator 435, 440 with an enable pin 445, 450, and the driving of this pin with both a pushbutton 490, 495 and an output of the respective microprocessor 425, 430, allows the control system 410 to fully shut down when not in use—thereby consuming very little power when not needed. When needed, a simple push of the associated pushbutton 490, 495 activates (wakes up) the microprocessor, whereafter it will perform the required tasks and remain active as long as necessary.

Power consumption can be further minimized by powering peripheral devices such as the display 475 of the hand held controller 420 or the pressure sensor 465 of the vacuum control assembly 415 only when the associated microprocessor 425, 430 is active. Power consumption can be even further minimized by powering such peripheral devices with separate regulators that can be switched on and off by the microprocessors 425, 430 so that they are operative only when necessary.

By linking the output of the pushbuttons 490, 495 respectively associated with the enable pins 445, 450 of the regulators 435, 440 to an input of the associated microprocessor 425, 430, the pushbuttons can be used to perform multiple functions. In addition to enabling a power supply and starting a microprocessor, one such additional function might include communicating with a microprocessor once the microprocessor is activated. For example, a simple press of a pushbutton 490, 495 may place the associated microprocessor in automatic mode, which thereby acts to control the vacuum level within a prosthetic socket until a patient removes the prosthesis and/or the control system otherwise determines that automatic control is no longer needed. Once such a determination is made, the control system can shut down to conserve power.

In another wireless communication enabled embodiment, a transmitter/receiver 504 may be integrated into a communication device having a computer compatible interface, such as a serial or USB interface. This design would allow the use of a computer's (e.g., a PC, laptop, pen computer, PDA, smart phone, etc.) display and computational capabilities. More particularly, the communication device could be connected to a computer and thereafter used to wirelessly communicate with the evacuation device. This would be especially useful to a practitioner, who could then easily observe variations in a user's socket pressure through a step, and from step to step, so as to evaluate the function of the evacuation device. A practitioner could also adjust the evacuation device settings, and then save the settings to a hard disk or other storage medium.

Obviously, these are just a few examples of the types of wireless communication devices that may be used in conjunction with an evacuation device of the present invention. Such wireless communication devices could also be used to interact with an evacuation device in more complex ways, such as in troubleshooting and programming, for example. It is intended that all interactions capable of being performed locally could also be performed using a wireless link.

In another modification of an evacuation device of the present invention, the associated control system can be removed from the prosthesis to a remote location, preferably to a hand held device such as that described above. Placing the control system in a hand held or other remote controller may allow for the installation of simple and stable firmware at the location of the vacuum pump and would minimize the likelihood that future upgrades to the vacuum components located in/on the prosthesis will be required. All software upgrades and reconfigurations could then be made by reprogramming or replacing the handheld device—without having to access the actual prosthesis. Further, any potential time lag associated with the use of a hand held remote controller can be overcome by running the vacuum pump at slow speed—which would have the added benefit of reducing noise.

With respect to the power consumption of any control system of the present invention—including the exemplary control systems described above—it should be noted that several very low power consumption implementations of a functional control system can be accomplished by using components from companies such as Cypress Semiconductor Corporation, headquartered in San Jose, Calif. For example, this company features a line of mixed-signal array with on-chip controller devices, which are referred to as Programmable System-on-Chip (PSoC) devices. These PSoC devices are designed to replace multiple traditional microcontroller-based system components with a lower cost single-chip programmable component. It has been determined that the Cypress model CY8C20234 PSoC is particularly well-suited for an application such as the present invention due to its small size and very low power consumption—although other such components may also prove acceptable.

It can be understood that in versions of the present invention wherein an evacuation device is not provided with self-charging capabilities, or wherein a user wearing a prosthetic limb having a self-charging capable evacuation device is non-ambulatory for an extended period of time, it is possible to discharge the power source(s) to an unacceptable level. As such, it is desirable that an evacuation device of the present invention be equipped with a means to notify the user of a low power state and/or to take action(s) directed to preserving the power remaining in the power source.

One method of alerting a user to a low power state is by cycling the vacuum pump. That is, by repeatedly turning the vacuum pump on and off during the evacuation process, additional vibration and noise will be generated. While such cycling will actually increase power consumption, the additional vibration and noise can serve as a cue to the user that there is a problem and thus allow the user to charge the system before the power storage is completely depleted. A user may be similarly alerted to a low power situation by running the vacuum pump motor at a higher speed than normal. This would increase motor and/or vacuum pump noise, helping to alert the user is aware to the low power situation.

Upon detection of a low power state, a reduction in power consumption can be achieved in several ways. First, reducing the required vacuum level can be practiced. This method may be employed directly by a user with a manually operable evacuation device, or automatically by a microprocessor controlled device. An automatic reduction in vacuum level may also serve to notify the user of a low power situation.

With respect to evacuation devices of the present invention where such are present, the wireless (e.g., radio) link may be disabled once a low power state is detected. Although minimal, such a radio link does draw some power from the power source when enabled. Disabling the wireless link would also force the user to manually activate the evacuation device, thus making the low power state very apparent.

Yet another method of conserving electric power would be to disable the automatic control system, if present. This would prevent the possibly frequent cycling of the evacuation device, especially if the user's activity level is increasing. This action would also force the user to interact with the evacuation device in an alternate fashion that would make the low power condition apparent. Disabling the automatic control system could also allow a user to temporarily disable the evacuation device if the user's current activity level does not necessitate vacuum suspension—thereby preserving power to adjust the vacuum level should the user's activity level change.

Other means of alerting a user to a low power condition are certainly also possible. For example, a visual and/or audible alert may be employed, such as through the use of the LED or audio transducer interfaces described above. Additionally, a vibrator could also be used to communicate a low power condition to the user.

As mentioned previously, sensors, a microprocessor, and other devices may be associated with an evacuation device to form a more advanced prosthetic evacuation system. Such systems may provide for a number of operational modes that offer various advantages in function, convenience, and privacy.

One such operational mode is a multi-speed vacuum mode. At lower levels of power consumption, the vacuum pump motor operates at a reduced level of performance, but also at a reduced noise level. Therefore, in this multi-speed vacuum mode of operation, the user may choose between one of several predetermined levels of vacuum pump performance—with lower performance levels producing less noise and higher performance levels producing more noise. Thus, for example, if the user is in a noise sensitive environment (e.g., the theater, a library, etc.) and their activity level is relatively low, the user may choose a lower performance level to minimize noise. If noise is of little or no concern, then the user might select a higher performance level.

In addition to vacuum pump performance level selection by the user, another way to take advantage of the multi-speed vacuum mode of operation would be to use a level of activity monitor, as described above. Such a level of activity monitor could be used to detect the level of activity of the user and to subsequently adjust the performance of the vacuum pump to an appropriate level. This would have the additional advantage of reducing power consumption when the user is substantially sedentary.

An evacuation device of the present invention may also be used to assist with doffing (removal) of the prosthesis to which it is installed. When removal is desired, the user first typically removes a sealing sleeve, if present, and subsequently releases the vacuum in the socket by either placing a tool therein to open a passageway along the socket interior or by opening or otherwise activating an air valve. With the vacuum released, the prosthesis can then be removed from the residual limb. To assist with the removal process, an evacuation device of the present invention may employ a reversible vacuum pump or a pump coupled with a directional flow control valve to pump air back into the distal end of the socket and encourage its dislodgement from the residual limb. Alternatively, an evacuation device of the present invention may use two pumps; one to evacuate the socket during donning of a prosthesis and one to pressurize the socket during doffing of the prosthesis.

It is contemplated that a system capable of both evacuating and pressurizing a socket could also be used to in effect massage a residual limb by alternatingly creating higher and lower levels of socket pressure. Limb massage can beneficially function to increase perfusion and to force excessive fluid from the residual limb.

In addition to simply evacuating a prosthetic socket to impart suction suspension to a prosthesis, an evacuation device of the present invention can also have therapeutic uses. Amputees are often the victims of chronic wounds that seemingly will not heal. These wounds are sometimes the result of operations, and sometimes result from pressure sores. One of the dilemmas frequently faced by amputees is how to let their stump heal when its use is often necessary to their daily activities. While this dilemma is not unique to upper or lower limb amputees, it may be more problematic for lower limb amputees because they must rely on their residual limbs for ambulation and because their residual limbs are generally subjected to more forces and pressures than are those of upper limb amputees.

Research since about 1993 has indicated that sub-atmospheric pressure can be of benefit to the healing of chronic wounds. Blood flow has been found to be augmented by treatment at reduced pressures of around 125 mmHg. Healing has been shown to be further improved by cycling the reduced pressure; such as by repeatedly applying vacuum for approximately 5 minutes, removing the vacuum for 2 minutes, and repeating.

An evacuation device of the present invention can be used with a sealable socket to provide such a vacuum therapy regimen. The socket may be for treatment use only and may be disposable to obviate any concerns relating to the seepage of wound fluids during treatment. Such a socket may be especially useful for the treatment of new amputees. Alternatively, the socket may be part of a prosthesis. When incorporated into the stump socket of a prosthesis, the evacuation device may be programmed to enter a therapy mode when the amputee is inactive. This may be useful when the amputee has a wound(s) or other condition(s) that will benefit from vacuum therapy.

In this embodiment of the present invention, the evacuation device is programmed or otherwise set to achieve the desired vacuum level when operated. The evacuation device is further programmed to cycle on and off in order to repeatedly apply and release the vacuum, and to maintain the vacuum level for the necessary time—whatever that time is determined to be.

In conjunction with the above discussion, it is worth noting that one of the primary causes of sores on a residual limb is excessive motion of the residual limb within a prosthetic socket. An evacuated socket helps to maintain residual limb volume, thereby greatly reducing the tendency of the residual limb to move within a prosthetic socket. However, it is difficult to know what level of vacuum is actually necessary for a given patient at a given activity level, on a specific day. To help make such a determination, a residual limb motion sensor can be integrated into a prosthetic socket, and used to adjust the vacuum level therein. If motion over some period of time is too high, more vacuum is drawn. If the vacuum level has been maintained, but the user's activity level has declined, the vacuum level can be slowly reduced until motion is detected. The vacuum level can then be increased as necessary until the motion ends or is maintained at a level for which the current vacuum level is appropriate. Over time, a map of activity level vs. pressure (vacuum level) can be constructed and referenced to allow for quicker vacuum adjustments.

Several types of sensors can acceptably serve as the motion sensor described above. For example, the motion sensor may be comprised of one or more Hall sensors placed in the base or wall of a prosthetic socket and one or more small magnets fastened to the tip or side of a prosthetic liner worn over the residual limb. Alternatively, the motion sensor may be comprised of a mutual inductance device that measures the mutual inductance between a coil in the base of a prosthetic socket, and a small coil placed on the tip of a prosthetic liner worn over the residual limb. In another embodiment, the motion sensor may be comprised of an ultrasonic sensor that is tuned to detect a small metal plate mounted on the tip of a prosthetic liner worn over the residual limb. Placing this sensor in the prosthetic socket could directly detect a residual limb or prosthetic liner. In yet another embodiment, the motion sensor may be comprised of a force sensor placed in the prosthetic socket or liner or an instrumented lanyard attached to the liner. Intermittent contact of the residual limb with the force sensor will indicate the occurrence of residual limb motion within the socket.

In addition to collecting data on vacuum level and motion, a microprocessor associated with the present invention can be configured to collect other data of interest, including for example, and without limitation, the amount of time that the vacuum pump(s) are active, the amount of time the control system is in manual mode vs. automatic mode, the level of battery/capacitor charge, the number and frequency of leaks detected, the amount of time that the prosthesis has been worn, temperature (inside or outside the socket), etc. This data can then be used for a variety of purposes, such as service scheduling, warranty issues, to detect operational changes that might indicate and justify modification or replacement of the prosthesis, and others. For instance: (a) an increase in vacuum level fluctuations or in motion between the limb and socket over a period of time might indicate changes in residual limb shape that may require the fabrication of a new socket; (b) an increase in activity level associated with vacuum level fluctuations, or motion between the limb and socket over a period of time when leakage did not increase might indicate changes in activity level that may justify new prosthetic components that are appropriate for the increased activity level; (c) an increase in leak detection events may indicate that sealing elements require replacement; and (d) a decrease in pump usage, vacuum level fluctuations, or motion between the limb and socket over a period of time may indicate reduced usage of the limb due to discomfort or health problems, requiring prosthesis adjustment, replacement, or other intervention. Pump usage data can also be used to determine when servicing or replacement of the pump is required.

While various embodiments of the present invention have been illustrated primarily with respect to the case of lower limb prostheses (more primarily, below knee prostheses), the present invention also applies to above knee lower limb prostheses and upper limb prostheses. Furthermore, additional advantages and modifications will readily appear to those skilled in the art and are considered to be within the scope of the present invention.

Therefore, while certain embodiments of the present invention are described in detail above, the scope of the invention is not to be considered limited by such disclosure, and modifications are possible without departing from the spirit of the invention as evidenced by the following claims:

What is claimed is:

1. A wireless control system for a prosthetic device, comprising:
   (1) an evacuation device located on or in a prosthesis, wherein the evacuation device comprises:
      an evacuation device microprocessor;
      a vacuum pump connected to a socket of the prosthesis and in communication with the evacuation device microprocessor, wherein the evacuation device microprocessor automatically activates the vacuum pump to adjust vacuum level of the socket;
      a pressure sensor in communication with the microprocessor of the evacuation device, wherein the pressure sensor monitors the vacuum level of the socket;
      an evacuation device wireless transceiver in communication with the evacuation device microprocessor; and
      a regulator in communication with the evacuation device microprocessor, the regulator comprising an enable pin wherein the enable pin is driven to selectively cause the evacuation device microprocessor to be active or inactive;
   (2) a hand held controller comprising:
      a hand held controller microprocessor; and
      a hand held controller wireless transceiver in communication with the hand held controller microprocessor and wirelessly linked to the evacuation device wireless transceiver,
   wherein the hand held controller causes the vacuum pump of the evacuation device to adjust the vacuum level of the socket and to receive parameters associated with the vacuum level of the socket via wireless communications with the evacuation device.

2. The wireless control system of claim 1, wherein the evacuation device wireless transceiver is integrated into the evacuation device microprocessor, and wherein the hand held controller wireless transceiver is integrated into the hand held controller microprocessor.

3. The wireless control system of claim 1, wherein the hand held controller is a fob.

4. The wireless control system of claim 3, further comprising an electronic display on the hand held controller, wherein the electronic display is in communication with the hand held controller microprocessor and is operable to display the parameters associated with the vacuum level of the socket.

5. The wireless control system of claim 4, wherein the electronic display is a liquid crystal display (LCD) type electronic display.

6. The wireless control system of claim 1, wherein the evacuation device comprises a pushbutton operatively connected to the enable pin of the regulator, wherein actuation of the pushbutton drives the enable pin and causes the evacuation device microprocessor to be active.

7. The wireless control system of claim 6, wherein the pushbutton is operatively connected to an input of the evacuation device microprocessor.

8. The wireless control system of claim 6, wherein the enable pin of the regulator is operatively connected to an output of the evacuation device microprocessor, wherein the evacuation device microprocessor automatically:
   determines that control of the vacuum pump is not needed; and
   upon determining that control is not needed, drives the enable pin of the regulator and cause the evacuation device microprocessor to be inactive.

9. The wireless control system of claim 1, wherein the evacuation device microprocessor automatically:
   determines that control of the vacuum pump is not needed; and
   upon determining that control is not needed, causes the pressure sensor to be switched off.

10. A wireless control system for a prosthetic device, comprising:
    (1) an evacuation device located on or in a prosthesis, wherein the evacuation device comprises:
       an evacuation device microprocessor;
       a vacuum pump connected to a socket of the prosthesis and in communication with the evacuation device microprocessor, wherein the evacuation device microprocessor automatically activates the vacuum pump to adjust vacuum level of the socket;
       an evacuation device wireless transceiver in communication with the evacuation device microprocessor; and
       an evacuation device regulator in communication with the evacuation device microprocessor, the evacuation device regulator comprising an enable pin wherein the enable pin is driven to selectively cause the evacuation device microprocessor to be active or inactive;
    (2) a hand held controller comprising:
       a hand held controller microprocessor; and
       a hand held controller wireless transceiver in communication with the hand held controller microprocessor and wirelessly linked to the evacuation device wireless transceiver,
       a hand held controller regulator in communication with the hand held controller microprocessor, the hand held controller regulator comprising an enable pin wherein the enable pin of the hand held controller regulator is driven to selectively cause the hand held controller microprocessor to be active or inactive,
       wherein the hand held controller causes the vacuum pump of the evacuation device to adjust the vacuum level of the socket via the wireless communications with the evacuation device.

11. The wireless control system of claim 10, wherein the evacuation device wireless transceiver is integrated into the evacuation device microprocessor; and the hand held controller wireless transceiver is integrated into the hand held controller microprocessor.

12. The wireless control system of claim 10, wherein the hand held controller is a fob.

13. The wireless control system of claim 10, wherein the hand held controller comprises an electronic display in communication with the hand held controller microprocessor, and wherein the electronic display is a liquid crystal display (LCD) type electronic display.

14. The wireless control system of claim 13, wherein the hand held controller microprocessor automatically:
   determines that control of the vacuum pump is not needed; and
   upon determining that control is not needed, drives the enable pin of the hand held controller regulator and causes the hand held controller microprocessor to be inactive.

15. The wireless control system of claim 10, wherein the evacuation device comprises an evacuation device pushbutton operatively connected to the enable pin of the evacuation device regulator, such that actuation of the evacuation device pushbutton drives the enable pin of the evacuation device regulator and causes the evacuation device microprocessor to be active; and wherein the hand held controller comprises a hand held controller pushbutton operatively connected to the enable pin of the hand held controller regulator, such that actuation of the hand held controller pushbutton drives the enable pin of the hand held controller regulator and causes the hand held controller microprocessor to be active.

16. The wireless control system of claim 15, wherein output of the evacuation device pushbutton is operatively connected to an input of the evacuation device microprocessor, and output of the hand held controller pushbutton is operatively connected to an input of the hand held controller microprocessor.

17. The wireless control system of claim 10, wherein the enable pin of the evacuation device regulator is operatively connected to an output of the evacuation device microprocessor, and wherein the evacuation device microprocessor automatically:
   determines that control of the vacuum pump is not needed; and
   upon determining that control is not needed, drives the enable pin of the regulator and cause the evacuation device microprocessor to be inactive.

18. The wireless control system of claim 17, wherein the enable pin of the hand held controller regulator is operatively connected to an output of the hand held controller microprocessor, and wherein the hand held controller microprocessor automatically:
   determines that control of the vacuum pump is not needed; and
   upon determining that control is not needed, drives the enable pin of the hand held controller regulator and causes the hand held controller microprocessor to be inactive.

19. A wireless control system for a prosthetic device, comprising:
   (1) an evacuation device located on or in a prosthesis, wherein the evacuation device comprises:
      a microprocessor;
      a vacuum pump connected to a socket of the prosthesis and in communication with the evacuation device microprocessor, wherein the microprocessor automatically activates the vacuum pump to adjust vacuum level of the socket;
      an evacuation device wireless transceiver in communication with the evacuation device microprocessor;
      a regulator in communication with the microprocessor, the regulator comprising an enable pin wherein the enable pin is driven to selectively cause the microprocessor to be active or inactive; and
      a pushbutton operatively connected to the enable pin of the regulator, wherein actuation of the pushbutton drives the enable pin and causes the microprocessor to be active, and wherein the evacuation device microprocessor automatically:
         determines when control of the vacuum pump is not needed; and
         upon determining that control is not needed, drives the enable pin of the regulator and cause the evacuation device microprocessor to be inactive
   (2) a hand held controller comprising a hand held controller wireless transceiver wirelessly linked to the evacuation device wireless transceiver, wherein the hand held controller causes the vacuum pump of the evacuation device to adjust the vacuum level of the socket via wireless communications with the evacuation device.

* * * * *